(12) United States Patent
Fern et al.

(10) Patent No.: US 9,339,219 B2
(45) Date of Patent: May 17, 2016

(54) DEVICES, SYSTEMS, AND METHODS RELATED TO ANALYTE MONITORING AND MANAGEMENT

(71) Applicant: Abbott Diabetes Care Inc., Alameda, CA (US)

(72) Inventors: Jonathan Fern, Alameda, CA (US); Mark P. Jesser, Austin, TX (US); Lynn Dixon, Fremont, CA (US); Jai Karan, Fremont, CA (US); Charles Wei, Fremont, CA (US); Matthew T. Vogel, Oakland, CA (US); Timothy S. Gasperak, Berkeley, CA (US); Kim Cullen, San Francisco, CA (US); Kim Ladin, Campbell, CA (US); Marc B. Taub, Mountain View, CA (US); Gary A. Hayter, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 14/954,457

(22) Filed: Nov. 30, 2015

(65) Prior Publication Data

US 2016/0081598 A1   Mar. 24, 2016

Related U.S. Application Data

(63) Continuation of application No. 13/091,557, filed on Apr. 21, 2011, now Pat. No. 9,198,623.

(60) Provisional application No. 61/327,023, filed on Apr. 22, 2010.

(51) Int. Cl.
*C12M 1/34* (2006.01)
*A61B 5/145* (2006.01)
*A61B 5/00* (2006.01)
*A61B 5/15* (2006.01)

(52) U.S. Cl.
CPC .......... *A61B 5/14532* (2013.01); *A61B 5/14546* (2013.01); *A61B 5/150358* (2013.01); *A61B 5/72* (2013.01); *A61B 5/742* (2013.01)

(58) Field of Classification Search
CPC ............. A61B 5/14532; A61B 5/7435; A61B 5/7475; A61B 5/0022; A61B 2560/045; A61B 5/743; A61B 2560/0295
See application file for complete search history.

(56) References Cited

U.S. PATENT DOCUMENTS

| | | | |
|---|---|---|---|
| 3,907,503 | A | 9/1975 | Betts et al. |
| 4,545,382 | A | 10/1985 | Higgins et al. |
| 4,711,245 | A | 12/1987 | Higgins et al. |
| 5,262,035 | A | 11/1993 | Gregg et al. |
| 5,262,305 | A | 11/1993 | Heller et al. |
| 5,264,014 | A | 11/1993 | Lannefors et al. |
| 5,320,725 | A | 6/1994 | Gregg et al. |
| 5,356,786 | A | 10/1994 | Heller et al. |

(Continued)

*Primary Examiner* — Shogo Sasaki
(74) *Attorney, Agent, or Firm* — Edward J. Baba; Bozicevic, Field & Francis LLP

(57) ABSTRACT

Analyte monitoring devices, systems, and methods are provided that relate to: enabling different application features on a data processing device for analyte monitoring devices with different analyte monitoring features; programming analyte monitoring devices in advance; personalizing an analyte monitoring device; graphically representing a remaining insulin level in a user body; and graphically representing analyte measurement related data for on-demand readings; protecting access to feature of an analyte monitoring device.

10 Claims, 18 Drawing Sheets

(56) References Cited

U.S. PATENT DOCUMENTS

| | | |
|---|---|---|
| 5,509,410 A | 4/1996 | Hill et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,414,684 B1 | 7/2002 | Mochizuki et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,676,816 B2 | 1/2004 | Mao et al. |
| 6,730,100 B2 | 5/2004 | Yamaguchi et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 6,942,616 B2 | 9/2005 | Kerr, II |
| 7,167,818 B2 | 1/2007 | Brown |
| 7,299,082 B2 | 11/2007 | Feldman et al. |
| 7,647,237 B2 | 1/2010 | Malave et al. |
| 7,811,231 B2 | 10/2010 | Jin et al. |
| 2002/0132363 A1 | 9/2002 | Rehm |
| 2003/0219713 A1 | 11/2003 | Valencia et al. |
| 2006/0010098 A1 | 1/2006 | Goodnow et al. |
| 2006/0031094 A1 | 2/2006 | Cohen et al. |
| 2008/0119710 A1 | 5/2008 | Reggiardo et al. |
| 2008/0139910 A1 | 6/2008 | Mastrototaro et al. |
| 2009/0164190 A1 | 6/2009 | Hayter et al. |
| 2009/0164239 A1 | 6/2009 | Hayter et al. |
| 2009/0164251 A1 | 6/2009 | Hayter et al. |
| 2009/0221890 A1 | 9/2009 | Saffer et al. |
| 2010/0082364 A1 | 4/2010 | Taub et al. |
| 2010/0198034 A1 | 8/2010 | Thomas et al. |
| 2010/0287477 A1 | 11/2010 | Maetzler et al. |
| 2012/0269681 A1 | 10/2012 | Tatsutani et al. |

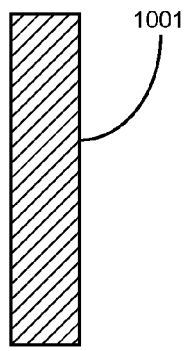 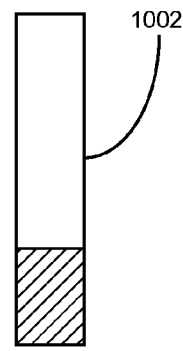
FIG. 10A              FIG. 10B
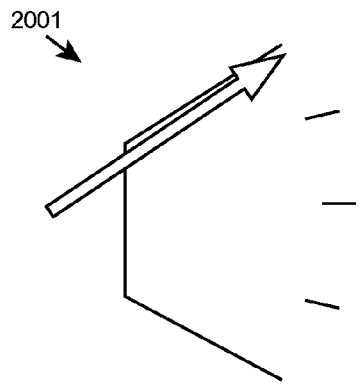 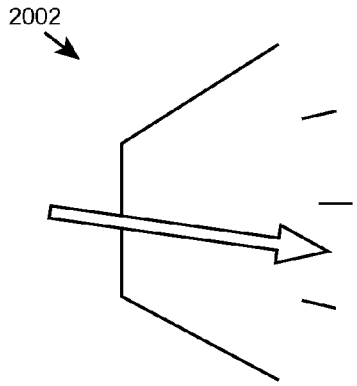
FIG. 11A              FIG. 11B
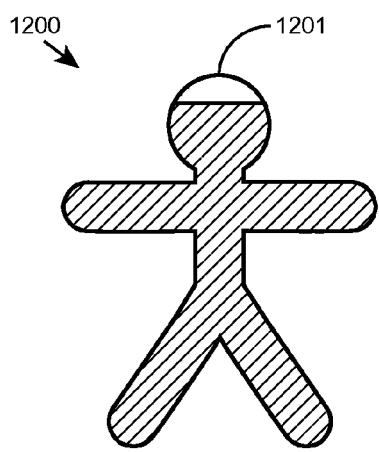 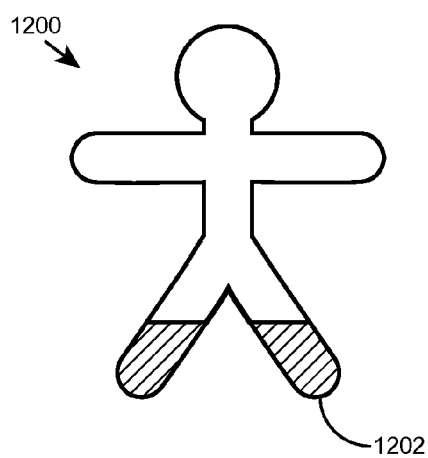
FIG. 12A              FIG. 12B

DEVICES, SYSTEMS, AND METHODS RELATED TO ANALYTE MONITORING AND MANAGEMENT

PRIORITY

This application is a continuation of U.S. application Ser. No. 13/091,557, filed Apr. 21, 2011, now U.S. Pat. No. 9,082,778 which application claims the benefit of priority to U.S. Provisional Application No. 61/327,023, filed Apr. 22, 2010, which are hereby incorporated by reference in their entirety.

BACKGROUND

Analyte monitoring devices have been used as medical diagnostic devices to determine a level of analyte from a sample. One common application is blood glucose measurements for diabetics. The diabetic typically pricks his or her finger using a lancet. A droplet of exposed blood is applied to a sensor on a test strip which is placed in the analyte monitoring device (in this case a glucose meter). A reading appears on a display of the measuring device indicating the blood glucose level of the diabetic. Analyte monitoring devices may be used to receive analyte measurement readings over a period of time for purposes of monitoring a patient's status or progress.

BRIEF DESCRIPTION OF THE FIGURES

The subject matter of the present disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included are the following:

FIGS. 10A-10B illustrate an example graphical user interface element that functions as a fill-level indicator, according to some embodiments.

FIGS. 11A-11B illustrate an example graphical user interface element representing insulin remaining in a body, according to some embodiments.

FIG. 12A-12B illustrate a graphical element representing insulin in the body, according to certain embodiments.

DETAILED DESCRIPTION

Figure 1A:
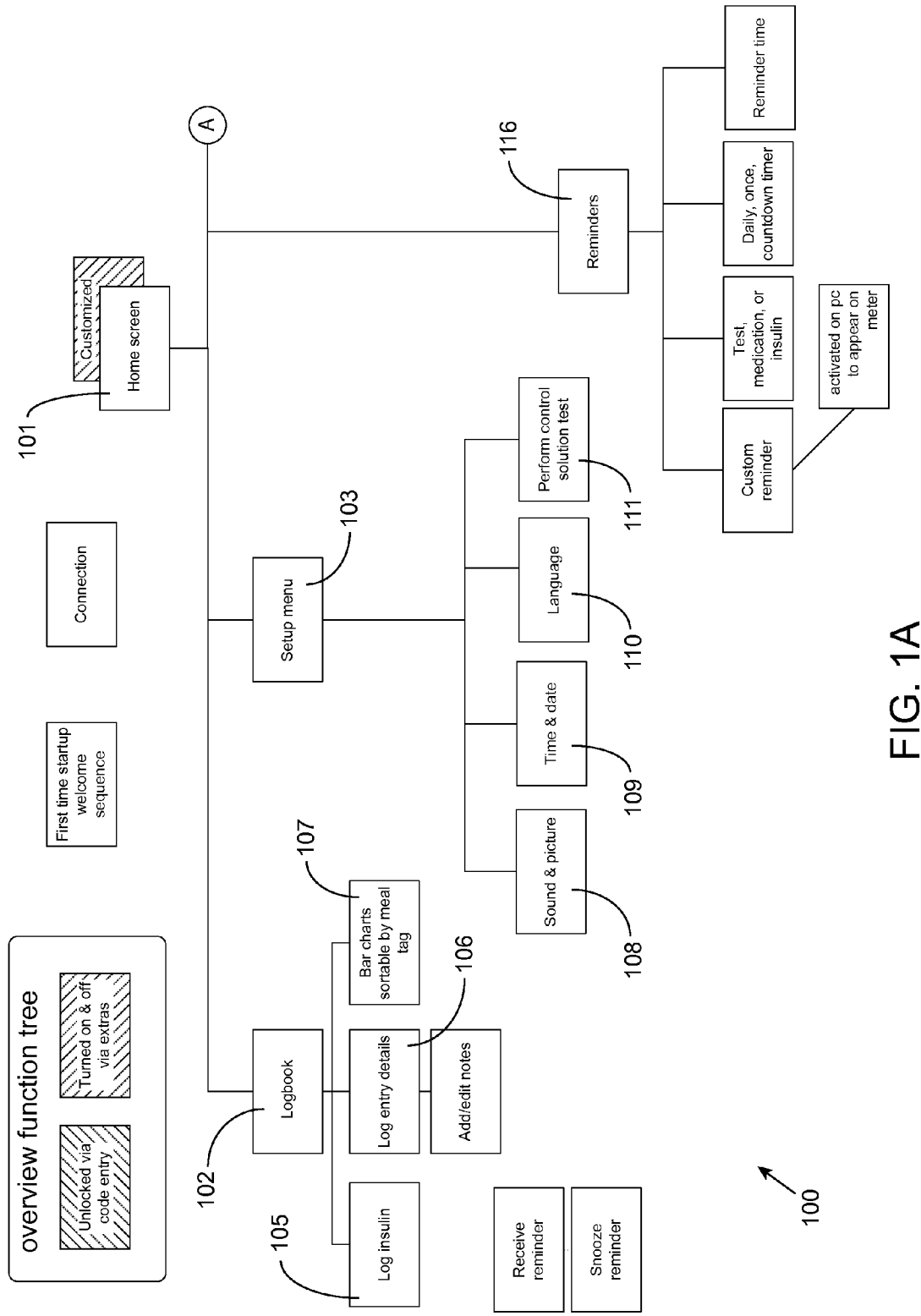
FIGS. 1A-1C illustrates a block diagram representing an overview of a user interface flow for an analyte monitoring device, according to some embodiments

Before the subject matter of the present disclosure is described, it is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which this present disclosure belongs. Although any methods and materials similar or equivalent to those described herein can be used in the practice or testing of the subject matter of the present disclosure, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a feature" includes a plurality of such features and reference to "the feature" includes reference to one or more features and equivalents thereof known to those skilled in the art, and so forth.

The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

User Interface for the Analyte Monitoring Device

In the present disclosure, various block diagrams, flowcharts, and graphical user interfaces (GUI) associated with an analyte monitoring device are discussed and illustrated. It should be understood that the specific embodiments discussed and shown are exemplary and that other embodiments may be implemented without compromising the underlying principles in the present disclosure. For example, all features shown in the exemplary embodiments are not necessarily required and may be combined, deleted, etc., in some situations without compromising the underlying principles in the present disclosure.

In some aspects, the analyte monitoring device stores software programs and applications in, for example, Flash memory, or other non-volatile memory. The software programs and applications that are installed and stored in memory in the analyte monitoring device provide for the user interface of the analyte monitoring device. The analyte monitoring device includes a control unit which may include any variety of processing devices—e.g., CPU, processor, microprocessor, microcontroller, etc. The control unit executes the various software programs and applications to provide the user interface to the analyte monitoring device.

In some aspects, the analyte monitoring device provides the necessary hardware and software to acquire analyte test measurements for a patient. The analyte monitoring device may include a test strip port to receive test strips and analyze any analyte samples present on the test strip. For example, the user may insert a test strip into the test strip port and then apply a sample of blood to the test strip so that the analyte monitoring device can measure the glucose levels of the sample. In some instances, the analyte monitoring device may receive analyte readings from another device—e.g., from an implantable sensor for glucose on demand (GoD) applications, and/or from continuous glucose monitoring (CGM) devices. In some embodiments, an adapter with one or more such capabilities may be coupled to the analyte monitoring device to provide the device with such capabilities.

In some aspects of the present disclosure, a user interface flow for an analyte monitoring device is provided. The user interface flow comprises various graphical user interfaces displayed on the analyte monitoring device and/or features/functions/settings available or accessible to the user. The user may navigate between various graphical user interfaces and/or accessing various features and functions of the analyte monitoring device.

It should be understood that the term "graphical user interface" is used broadly herein to represent any graphical interface element displayed on the display. For example, the graphical user interface may comprise a graphical icon, element, picture, video, text box, pop-up window, application window, home screen, etc. Furthermore, it should be understood that one or more GUIs may be implemented for various features, functions and/or settings. Further, different GUIs may be combined in some instances without compromising the underlying principles of the disclosure.

The analyte monitoring device may include a landing (e.g., a home screen) that is displayed on the display of the analyte monitoring device and functions as a starting point or relative starting point. From the home screen the user can navigate to any of the various GUI's to perform or access various functions and features of the device.

These branches of navigation may be accessed when the user activates trigger elements on the device. The trigger elements may be any variety of trigger elements—e.g., buttons, keys, toggle switches, wheels, arrows, etc. The trigger elements may be physical and tangible trigger elements located on the device (e.g., hardware buttons or keys on the housing or keyboard, etc.) and/or may be nontangible trigger elements (e.g., graphical user interface elements) displayed on the device. It should also be understood that the branches of navigation may be displayed on the home screen (e.g., as icons) and triggered by corresponding physical and tangible trigger elements on the housing of keyboard. For example, in certain embodiments, a touchscreen display is implemented and the trigger elements are icons displayed on the touchscreen. The trigger element is activated by the user touching the corresponding trigger element (e.g., icon). It should be understood that icons is used broadly herein to represent any text, image, video, graphic, etc. For example, the trigger element may be suggestive of its function or feature—e.g., an image of a gear representing a trigger element for accessing the setup menu, an arrow keys, check boxes, toggle switches, buttons (e.g., with identifying text or image inside), etc. It should be understood that the underlying principles of the present disclosure are not limited to a touchscreen implementation.

Figure 1B:
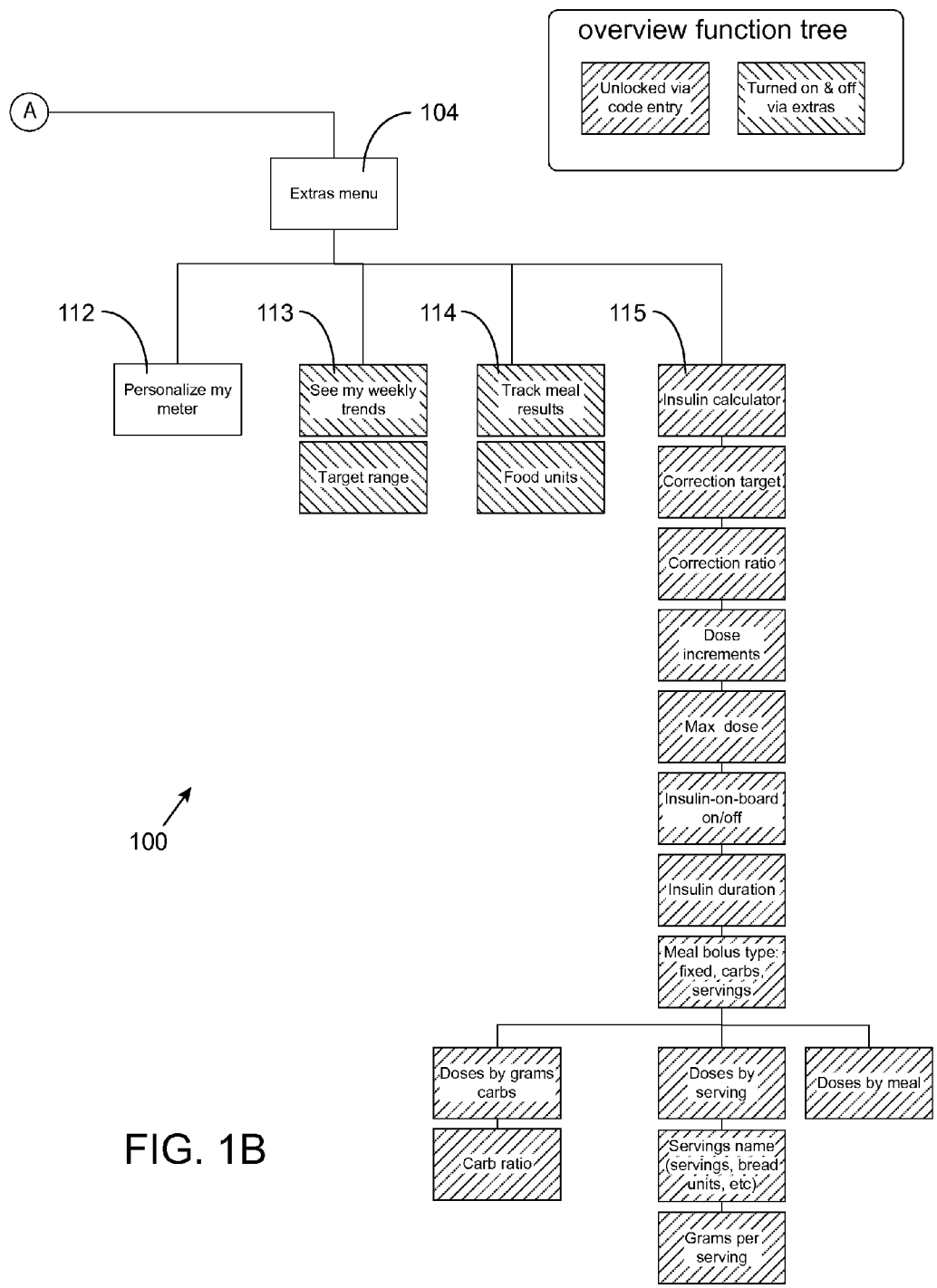
Figure 1C:
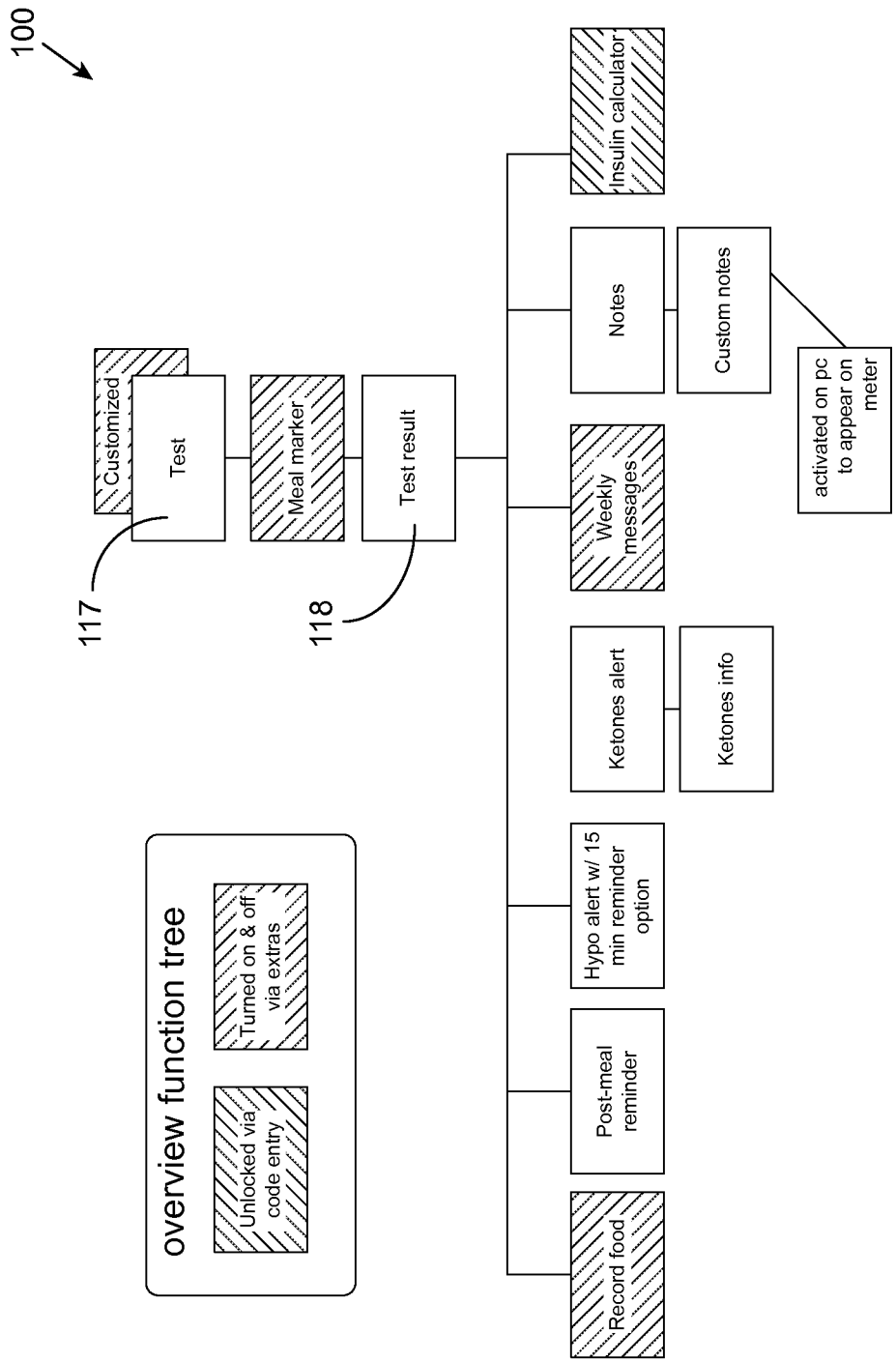

For example, FIGS. 1A-1C illustrate a block diagram representing an overview of a user interface flow for an analyte monitoring device, according to some embodiments. The block diagrams shown in each of FIGS. 1A-1B connect at the reference letters A.

Block diagram 100 is shown comprising a home screen 101 from which the user may navigate (e.g., via a trigger element on a touchscreen display or with buttons on the device) to logbook screen 102, setup menu 103, extras menu 104, and reminder screen 116. From logbook 102, the user may access other feature and functions, such as logging insulin 105, viewing log entry details 106, and viewing various charts and graphs 107. It should be appreciated that other features and functions may be available from logbook 102 in other embodiments.

Setup menu 103 enables a user to setup the device—e.g., adjust sound and graphics 108, set the time and date 109, set the language 110, and perform control solution tests 111. Further, from extras menu 104, the user may access various features and function related to personalizing the device 112, viewing statistical data 113 (e.g., trends, target ranges, etc.), viewing/controlling food data and settings 114, and viewing/controlling insulin related data and settings 115 (or other drug related data).

From reminders 116, the user may navigate to various features and function related to viewing and controlling various reminders (and alerts in some instances).

FIG. 1 also shows navigation from a test screen 117. As shown, after a test result 118 for a test measurement is generated, the user may access various feature and functions from the test result screen 118. It should be appreciated that, in some instances, the user may be automatically taken to another feature or function.

Again, it should be appreciated that the user interface flow provided in FIG. 1 is exemplary and should not be construed as limited to such example. Furthermore, for the sake of clarity and brevity, not all user interface screens and features and functions are described for FIG. 1. Further details regarding various example user interfaces that may be implemented with analyte monitoring systems is described in U.S. Provisional Patent Application Nos. 61/451,488, filed Mar. 10, 2011; 61/326,651, filed Apr. 21, 2010; and 61/327,023, filed Apr. 22, 2010, the entireties of which are incorporated herein by reference.

Figure 2:
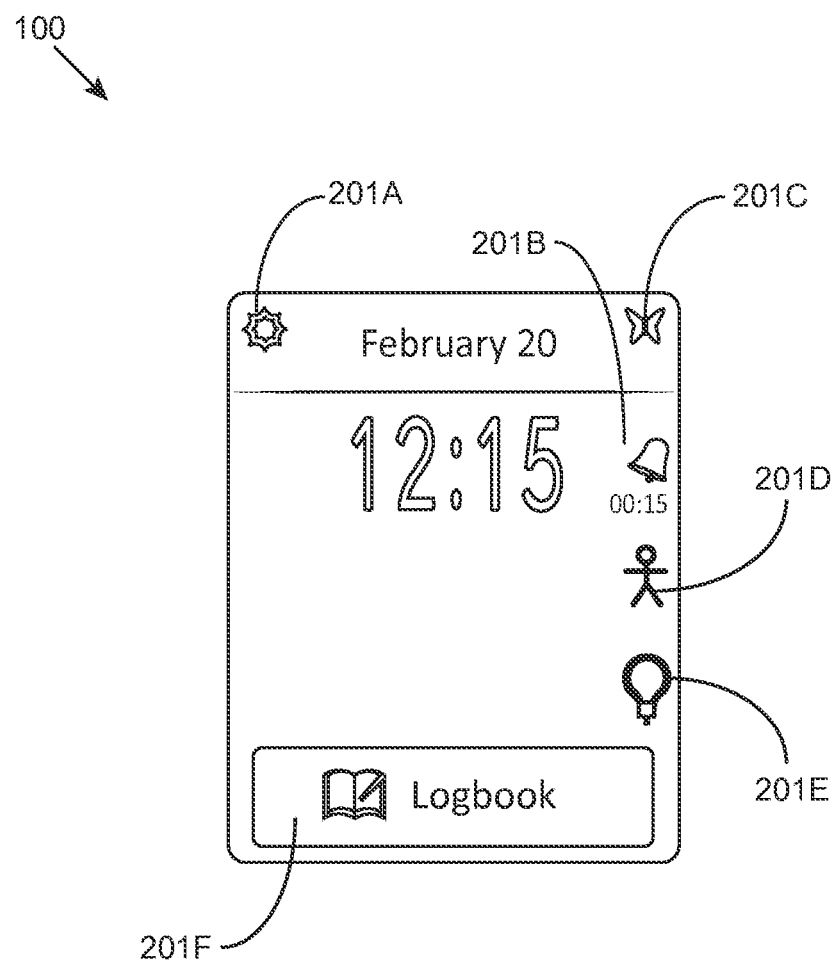
FIG. 2 illustrates a home screen, according to certain embodiments.

FIG. 2 illustrates a home screen, according to certain embodiments. Home screen 200 is shown comprising various trigger elements 201A-201F that can be activated by the user touching the trigger element on the touchscreen of the analyte monitoring device. For example, trigger element 201A navigates to a settings screen; trigger element 201B navigates to a reminders screen; trigger element 201C navigates to the extras screen; trigger element 201D navigates to an insulin in body screen; trigger element 201E is a feature that enables the user to turn a test strip port light on and off; and trigger element 201F navigates to a logbook screen.

When the meter is turned on, for example, the home screen may be presented for the user to access various GUI's, features, and functions of the device. In some instances, the home screen may include one or more formats. For example, a date format may be implemented and display the date and time on the home screen, such as shown in FIG. 2. It should be understood that other formats may be implemented. In some instances, as pointed out on page 5, a home screen may be customized—e.g., with a background image or customized text.

In some embodiments, the analyte monitoring device may include a test port and provide the capability to perform test measurements on a fluid sample. For example, a test strip may be received by the test port and a sample applied to the test strip. The analyte monitoring device performs a measurement reading on the sample and displays and/or stores the reading on the device.

In some aspects, the analyte monitoring device enables the user to add notes to provide a more comprehensive analysis at a later time. For example, these customized notes may provide additional details associated with measurement readings taken.

As stated before, the analyte monitoring device may specifically relate to glucose monitoring of patients (e.g., diabetics) in both clinical and home use environments. Patients that use long and/or short-acting insulin may use glucose measurement readings to estimate if insulin is needed and how much to use. The analyte monitoring device may include software programs for performing insulin dosage calculations with the analyte monitoring device. In some instances, the insulin calculation may take into account factors in addition to a current measurement reading or string of measurement readings. One or more of the following additional factors may also be taken into account—e.g., threshold maximum and minimum values, trending of measurement readings, times of tests (e.g., whether before and after meals and/or time since last meal, and/or times from last insulin dosage and/or amount of insulin remaining in the body), exercise, meals and food intake (e.g., carbohydrate values, anticipated carbohydrate values, bread units, serving size, etc.), etc. It should be appreciated that other factors may also be taken into account, and that the example factors are not limiting.

In some aspects, the analyte monitoring device may include insulin calculation features that are available and presented to the user. For example, in certain embodiments, the device may include insulin dosage calculation. For example, the analyte monitoring device may display various screens for entering user inputs regarding such factors and calculation, and then perform the calculation using those user inputs and displaying the calculated result associated with the suggested amount of insulin for the patient.

In some aspects, the analyte monitoring device may include settings (and/or configurations) and reminders features that are available and accessible to the user. For example, in some instances, user interfaces may be implemented associated with settings for the analyte monitoring device and reminders. In some instances, settings allow the user to adjust settings related to date and time, sounds and pictures, languages, control solution tests, etc. A wide range of reminders may be implemented for various purposes and should not be construed to be limited to these specific examples. One or more types of reminders may be implemented. For example, reminders relating to measurement tests may be implemented—e.g., to remind the user to perform test measurements at various times and/or upon occurrence of certain events, etc. Certain events may include, for example, measurement readings at or beyond threshold level, or projections of measurement readings at or beyond a threshold level. For example, reminders to take a measurement reading may be provided when a measurement level crosses an upper and lower threshold value (e.g., the upper and lower bounds of a target range). As another example, reminders to take a measurement reading may be provided when an upper and lower threshold level are projected to be crossed. In some instances, the reminder may not be provided until the time when the upper or lower threshold level was projected to be crossed. Furthermore, the reminders may be provided at various times. For example, upon the occurrence of the event, the reminder may be provided at a fixed time after the occurrence; at a user configured time after the occurrence; at a time based on the reader's actual projection that the threshold would have been crossed; at a time equal to the time horizon of a configurable projected alarm. In some instances, multiple thresholds may be implemented with the reminders being provided at different times for each. For example, a blood glucose threshold of 120 mg/dL may trigger a reminder to take another measurement in 15 minutes; another blood glucose threshold of 130 mg/dL may trigger a reminder to take another measurement in 5 minutes; and yet another blood glucose threshold of 150 mg/dL may trigger a reminder to take another measurement in 1 minute.

Furthermore, reminders relating to medication may be implemented—e.g., to remind the user to take medicine at various times and/or upon occurrence of certain events. Still further, reminders related to insulin may be implemented—e.g., to remind the user to take insulin at various times and/or upon occurrence of certain events. In some instances, additional and/or customizable reminders may be implemented in the analyte monitoring device. In some instances, the frequency (e.g., daily, once, etc) of the reminder and/or a countdown timer may be set.

Additional details regarding alarms and reminders may be found in U.S. Nonprovisional patent application Ser. No. 11/555,192, filed Oct. 31, 2006, the entirety of which is herein incorporated by reference.

It should be understood that alarms may also be implemented on the device and viewed/controlled by the user, in certain embodiments. The reminders/alarms may take the form of audio, visual, and/or haptic feedback (e.g., vibratory) reminders. For instance, the reminder may be a particular GUI that pops up on the display to remind the user of the particular reminder. The GUI may encompass the display or be a smaller "window" that pops up over a current GUI. The reminder could also include an audio and/or vibratory reminder instead of, or in addition to, the GUI. Furthermore, it should be appreciated that the various symbols or icons may also be implemented in place of a pop up window or full screen GUI. The user may also take various actions upon being reminded—e.g., dismiss, snooze, confirm, etc.

Various patterns and messages may be implemented in certain embodiments to provide additional information to the user and/or physician. Patterns may include, for example, patterns in the data acquired from the analyte monitoring device. For instance, measurement reading patterns over various time periods and target ranges may be identified. In some instances, the patterns may relate to measurement reading patterns associated with various events (e.g., meals, exercises, insulin administration, etc.).

Messages may be displayed on the analyte monitoring device to inform the user of a wide variety of purposes. For example, in some instances, the messages are used to convey identified patterns to the user. For example, the user may receive a message via a message icon such as a suggestive 'envelope' icon, and may then access the message and information regarding one or more patterns. In some instances, the patterns and/or messages feature may be activated and deactivated by the user and/or physician.

In some aspects of the present disclosure, the analyte monitoring device may enable the user to personalize the analyte monitoring device using the analyte monitoring device. Personalization may include, for example, setting audio, visual, and/or haptic feedback (e.g., vibratory) themes for the analyte monitoring device and GUIs. For example, customized sounds, images (e.g., background images, icons, etc.), video, vibration patterns, etc. may be set by the user. In some instances, the user is presented with default options that may be chosen. In some instances, the user may upload various personalizations (e.g., images, sounds, etc.) to the device. In some embodiments, the audio, visual, and/or vibratory theme may be presented during a waiting period when performing a test measurement.

Figure 3A:
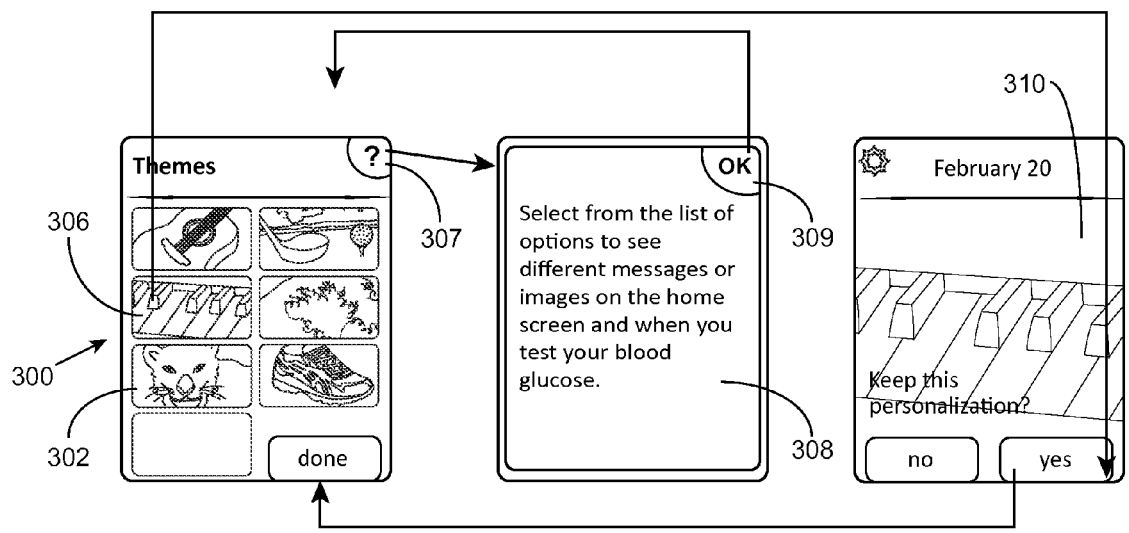
FIG. 3A illustrates a flowchart for personalizing an analyte monitoring device, according to certain embodiments.

FIG. 3 illustrates a flowchart for personalizing an analyte monitoring device, according to certain embodiments. A personalization screen 300 is shown displaying six pre-installed background images 301-306. In other embodiments, one or more uploaded background images may be displayed as well. The personalization screen 300 may be accessed in various manners—e.g., via an extras menu on the home screen. A help trigger element 307 is shown on the personalization screen 300. If activated by the user, the trigger element 307 navigates to the help screen 308 that provides additional information regarding the personalization screen 300. Trigger element 309 navigates back to the personalization screen 300. Upon selection of a pre-installed background image—e.g., background image 301—a confirmation screen 310 is displayed that includes the background image 301 displayed in the background. Upon user confirmation, the device is configured with the background image 301 displayed. In other embodiments, the device is configured to display the background image 301 when waiting for a measurement result during a test measurement.

In certain embodiments, the personalizing of the analyte monitoring device comprises configuring the analyte monitoring device to display a user selected name—e.g., as a banner on the background.

In certain embodiments, the analyte monitoring device comprises a housing, a strip port coupled to the housing, an output display coupled to the housing, a processor coupled to the housing, and memory operably coupled to the housing and electrically coupled to the first processor. The memory includes instructions stored therein for personalizing the analyte monitoring device.

Figure 3B:
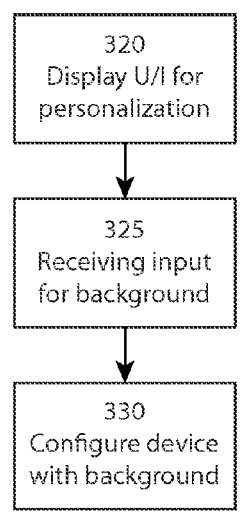
FIG. 3B illustrates an example block diagram for a method that is performed when the instruction are executed by the processor, according to certain embodiments.

FIG. 3B illustrates an example block diagram for a method that is performed when the instruction are executed by the processor, according to certain embodiments.

At block 320, a user interface is displayed on the output display. The user interface enables a user to personalize the analyte monitoring device—e.g., to configure the analyte monitoring device to display a user selected background image.

At block 325, the user selects a background image. In some embodiments, a plurality of pre-installed background images is displayed on the output display for the user to select from. In other embodiments, the user may upload a separate background image—e.g., from a storage device or from the internet, for example.

At block 330, the device is configured to display the user selected background image. In some embodiments, the background image is displayed on the home screen, for example. In other embodiments, the background image is displayed during a waiting period for an analyte measurement.

In some aspects of the present disclosure, the analyte monitoring device may enable the user to log food and/or view logged food data with the analyte monitoring device. In some instances, the capability to log food may be activated by the user or physician to provide a more comprehensive view of user data. For example, in some instances, the user may be provided with the capability to log food after test measurements.

In some aspects, the analyte monitoring device provides the capability to setup and/or adjust the settings of the insulin calculation feature. In some instances, setup may include, for example, one or more of the following: an introduction or short tutorial that is presented to the user; a lock feature to lock the calculator settings when complete; adjustment and/or setting of a target range, adjustment and/or setting of a correction range, adjustment and/or setting of a correction factor, adjustment and/or setting of dose increments, adjustment and/or setting of a maximum dose, adjustment and/or setting of a insulin duration; setup of a meal calculator; setup of a servings calculator; setup of bread units; setup of a carb calculator, etc. In some instances, the user may be presented with a GUI for reviewing, confirming, and/or editing the insulin calculation settings. In some instances, user interfaces are provided for locking the calculator settings of the analyte monitoring device.

In some aspects, the analyte monitoring device provides a logbook feature to log various data. The data may include measurement reading, data associated with the measurement readings, various events (e.g., meals, exercises, medication, insulin, etc.), etc., and may be recorded based on time and/or date of occurrence. Various data may be logged and stored in the device for later analysis and review. For example, in the user may be presented with the option to log results after measurements are taken. Additional notes and related information may be included and logged with the measurement to provide a more comprehensive view of the logged measurement. Furthermore, the user may access the logbook to review the data logged and/or review analysis of the data logged (e.g., statistical data, trends, patterns, averages, etc.). In some aspects, the analyte monitoring device may present the required interface to log insulin dosages and/or medicine intake. The insulin log may, for example, account for whether the insulin was long acting or rapid acting, the amount administered, time administered, etc.

In some embodiments, the device may be configured to automatically display one or more interfaces upon a first start or activation of the analyte monitoring device, according to some embodiments. The first start may take into account, for example, the language to be used, date, time, introduction or short tutorial, etc. For instance, the analyte monitoring device may prompt the user to enter, read, confirm, skip, etc., the information provided.

In some aspects, the analyte monitoring device provides an interface for setting carb data—e.g., setting carb ratios by time of day for the calculator setup of the analyte monitoring device. In some aspects, the analyte monitoring device provides an interface for setting correction factors—e.g., associated with setting correction factors by time of day, and setting correction factors adjusted for high blood glucose readings, for calculator setup of the analyte monitoring device.

In some instances, the analyte monitoring device may provide a warning and possible remedy. For example, if a user has a low blood sugar reading, the analyte monitoring device may display a warning that the user's blood sugar is low, and that suggested remedy may provide some relief—e.g., by taking a set amount of carbs, by suggesting a food product, etc. Some interface may be associated with setting units on the analyte monitoring device. In some instances, different features may be assigned different units independently.

In some instances, the analyte monitoring device may provide an interface for the user to account for insulin already taken by the user. In some instances, the analyte monitoring device will take into account whether the user has any insulin remaining in their body, and may include requests for user inputs to confirm previous administration times, amounts, etc.

User Interface for a Remote Data Processing Device

In some aspects, the analyte monitoring device may be communicatively coupled to a remote data processing device for management purposes. Remote device may include, for example, a personal computer, laptop, PDA, cellular phone, smartphone, set-top box, etc. The remote device may include, for example, a control unit including any variety of processor, microprocessor, microcontroller, etc. The remote device may also include a memory unit comprising non-volatile memory and volatile memory.

The term remote device is used herein to represent any device that is external to the analyte monitoring device. The remote device may require software to communicate and manage data from the analyte monitoring device. This user interface software (referred to herein as "remote device software" or "RD software" to distinguish it from the user interface software running on the analyte monitoring device) may be obtained from one or more methods such as downloading from the web, CD-ROM, memory stick, etc.

In some embodiments, the analyte monitoring device includes the RD software programs and/or applications to be run on the remote device. In some instances, the RD software may be configured to automatically launch when the analyte monitoring device is coupled to the computer. For example, the analyte monitoring device may include an installer program that is stored in non-volatile memory and executed when the analyte monitoring device is coupled to the remote device. The installer program may be executed when the user couples the analyte monitoring device to the remote device. The installer program may then initiate the launch of the RD software on the remote device.

In some embodiments, the RD software is not stored in non-volatile memory on the remote device. The RD software is stored on the analyte monitoring device and used to launch the RD software on the remote device is coupled to the analyte monitoring device.

In some embodiments, the RD software may be downloaded and stored in non-volatile memory on the remote device. For example, the RD software may be downloaded via a network connection (e.g., via an internet connection), by storage device (e.g., CD-ROM, memory stick, etc.), and/or downloaded from the analyte monitoring device. In some instances, the RD software is capable of being run even when the device is not coupled to the computer.

It should be understood that the RD software may be compatible with various hardware systems (e.g., PC, MAC) and various operating systems (e.g., Windows, MAC OS, Linux).

The analyte monitoring device may be communicatively coupled to the remote device via wired technologies. Example wired technologies may include, but are not limited to, the following technologies, or family of technologies: USB, FireWire, SPI, SDIO, RS-232 port, etc.

The analyte monitoring device may include, for example, a communication connector unit to permit wired communication and coupling to the remote device. The communication connector unit provides the capability to communicate with a remote device having an appropriate interface to operatively couple with the communication connector. In some embodiments, the communication connector is configured to communicate with a smartphone such as an iPhone or Blackberry.

The communication connector unit may be any variety of connection interfaces—e.g., male or female connection interfaces. Using USB as an example, the communication connector may be any of the variety of USB plugs or USB receptacles/ports. As USB receptacles are typically located on computer and other devices, a corresponding USB plug used as a communication connector unit will enable the analyte monitoring device to be plugged directly into the USB receptacle, avoiding the use of cables. In other instances, the appropriate USB receptacle may be used on the analyte monitoring device to enable communication using a USB cable (similar to many other devices such as digital cameras, cellular phones, smartphones, etc.).

It should be appreciated that the in some embodiments the analyte monitoring device may be communicably coupled to the remote device via wireless technology. In such instances, the analyte monitoring device may include corresponding transmitters, receivers, and/or transceivers. The analyte monitoring device may be configured to wirelessly communicate using a technology including, but not limited to, radio frequency (RF) communication, Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM), etc.

The functionality of the RD software launched on the remote device may include a variety of functions relating to, for example, data acquisition; data management; management of features, settings, configurations, etc., of the analyte monitoring device; generation, saving, transmitting, and/or printing of reports, management of updates (e.g., field updates to device firmware and RD software); access to training content, web-based content, web-based marketing; etc.

The RD software may be launched on a remote device and used by the user (e.g., the patient) and/or a health care provider (HCP) (e.g., physician, hospital staff, etc.). For example, the HCP and/or patient may use the RD software on a remote device to analyze the patient data, view and print reports, view and change device settings, update device firmware and application software, etc.

In some instances, the RD software may initiate a comparison between the time date on the analyte monitoring device and that on the remote device and/or remote time server accessed via an internet connection from the remote device. The RD software may account for discrepancies and take action accordingly. For example, thresholds may be set (e.g., 5 minute difference) and if the threshold is reached, the analyte monitoring device prompts the user with a warning, question, indicator, etc., to acknowledge the discrepancy and/or remedy the discrepancy (e.g., adjust the time on one of the devices). In some instances, a similar comparison may be performed by the RD software to account for other discrepancies between the analyte monitoring device and remote device—e.g., discrepancies between data logs, data values, stored files, device and/or user interface configurations and settings, etc. The appropriate action can then be taken or requested.

Various defaults and customized configurations and settings may be established for generating, printing, saving, exporting, etc., reports. For example, the various formats for the report may be established (e.g., layout, style, themes, color, etc.); various file types to save the report as (e.g., PDF, Word document, Excel spreadsheet, etc. In some instances, for example, the RD software may provide the user with the ability to export tab-delimited text files or XML exports of the meter data (e.g., including blood glucose, ketones, carbs, insulin, and event tags, etc.). In some instances, the RD software may enable the user to save, print, and/or export preferences, including favorite reports, target blood glucose ranges, auto save, auto print, color/black and white printing, device/software update settings for multiple devices, etc.

In some aspects, the RD software is used to control the configuration of the device and data from the device. This control may be utilized by the user and/or HCP. In some instances, the RD software shall provide access to one or more informative documents, trainings, tutorials, etc. For example, the RD software application may provide links or to manufacturer sponsored websites intended for any variety of purposes such as marketing and training content.

In some aspects, the RD software may include an update management function to help facilitate the detection, download, and installation of updates (e.g., firmware, informatics application updates, etc.) for the analyte meter device and/or the RD software. The updates may be detected and downloaded automatically in some instances (e.g., when an internet connection is active) and/or detected and downloaded upon user confirmation or request. In some instances, updates to the software shall also update its installation files stored on the device. Moreover, in some instances, when the device firmware is updated, required labeling/user documentation is also updated on the device. In some instances, when device firmware is updated, the existing device settings and testing history (e.g., blood glucose, insulin, carb data, etc.) is preserved.

Figure 4A:
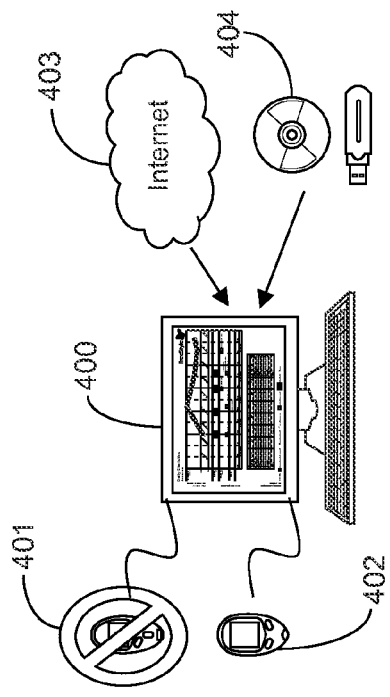
FIGS. 4A-4B illustrate a remote data processing device having RD software that enables it to operate with one type of analyte monitoring device but not another type of analyte monitoring device.
Figure 4B:
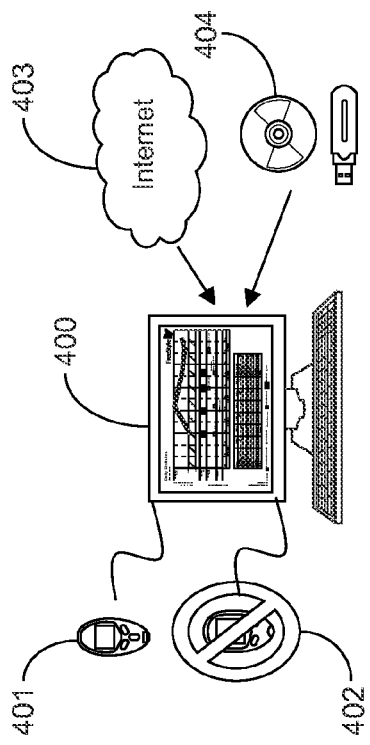

FIGS. 4A-4B illustrate a remote data processing device having RD software that enables it to operate with one type of analyte monitoring device but not another type of analyte monitoring device. Remote data processing device 400 has RD software installed on it. The software loaded onto the device 400 via the internet 403 or a memory device 404.

In FIG. 4A, the device 400 is enabled by the RD software to communicate with a coupled analyte monitoring device 401 but not with a coupled analyte monitoring device 402. For example, device 402 may be a legacy device that requires different RD software. In FIG. 4B, the device 400 is enabled by a different RD software to operate with a coupled analyte monitoring device 402 but not with a coupled analyte monitoring device 401.

Figure 4C:
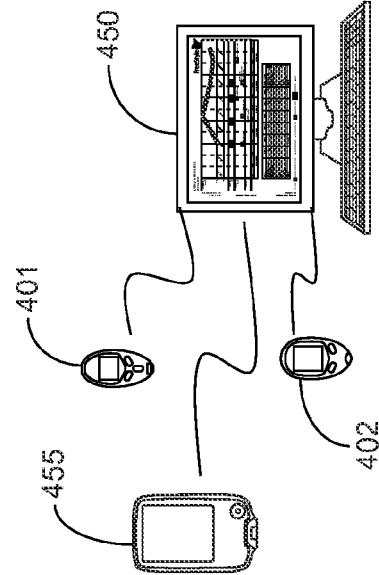
FIG. 4C illustrates a remote data processing device receiving RD software from an analyte monitoring device that enables the data processing device to operate with multiple types of analyte monitoring devices, according to certain embodiments.

FIG. 4C illustrates a remote data processing device receiving RD software from an analyte monitoring device that enables the data processing device to operate with multiple types of analyte monitoring devices, according to certain embodiments. Remote data processing device 450 is operably coupled to analyte monitoring device that has RD software installed on it. When connected, device 455 transfers the RD software to the device 450, which stores the software therein for execution. Device 455 may be, for example, a newer model of analyte monitoring device that has the RD software installed on it to enable compatibility with other types of analyte monitoring devices—e.g., legacy devices. In some instances, this RD software may be loaded onto the device 400 via the internet 403 or a memory device 404.

Figure 4D:
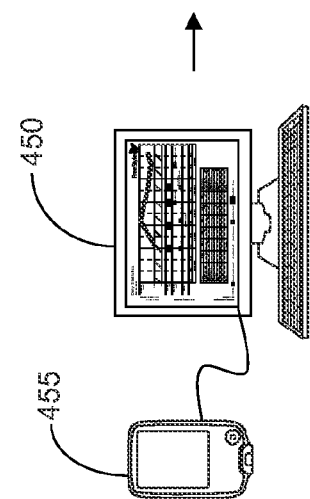
FIG. 4D illustrates device 455 operably connected to any one of the analyte monitoring devices 401, 402, and 455, according to certain embodiments.

FIG. 4D illustrates device 455 operably connected to any one of the analyte monitoring devices 401, 402, and 455, according to certain embodiments. It should be appreciated that all three devices are not necessarily connected at the same time, but are shown that way for illustrative purposes. For example, after device 455 loads the RD software on the device 450, the device 450 may operate with the analyte monitoring device 455. If the analyte monitoring device 455 is disconnected and another type of analyte monitoring device (e.g., device 401 or device 402) is connected, then the device 450 may operate with the other type of device (e.g., device 401 or device 402).

For example, in certain embodiments, all three devices 401, 402, and 455 may be able to perform blood glucose measurements, while only device 455 is able to utilize advanced functions, such as, but not limited to, insulin calculation (e.g., bolus and/or basal), ketone body measurements, personalization of the device, carb counting, etc.

Figure 4E:
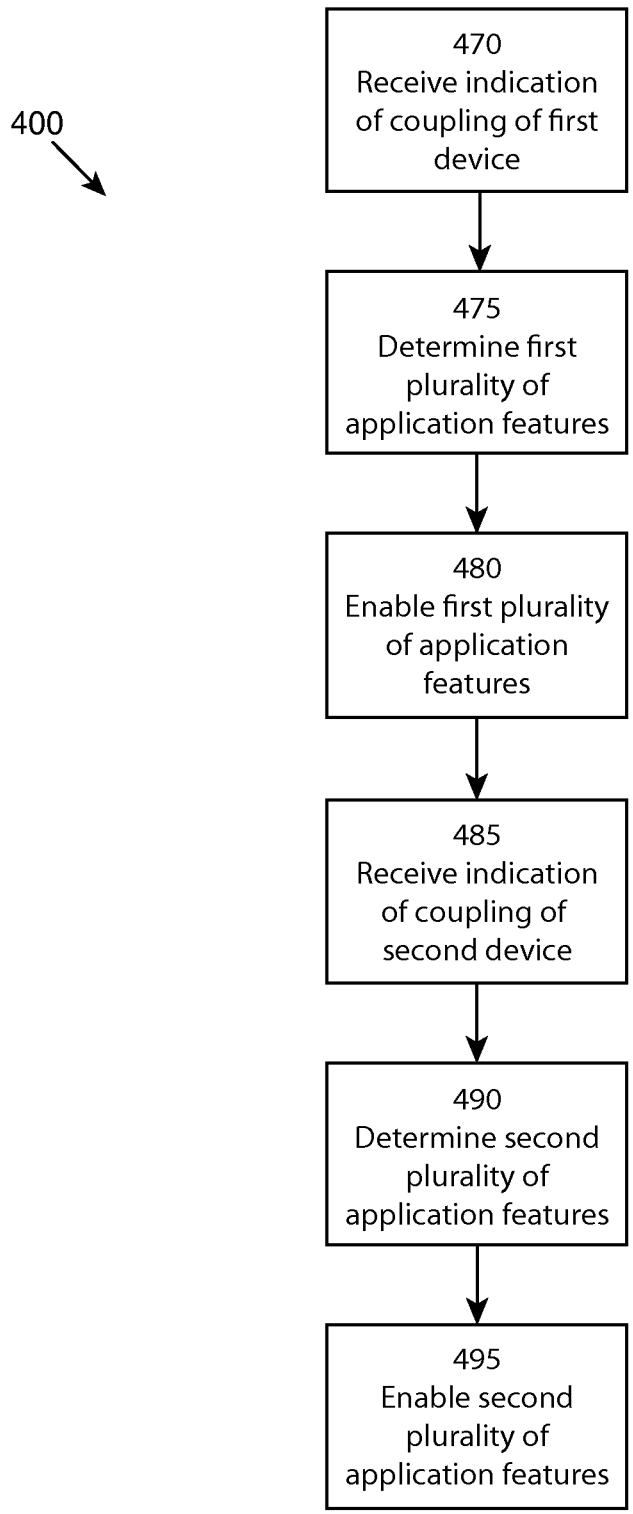
FIG. 4E illustrates a block diagram for a method of enabling different application features on a data processing device for analyte monitoring devices with different analyte monitoring features, according to certain embodiments.

FIG. 4E illustrates a block diagram for a method of enabling different application features on a data processing device for analyte monitoring devices with different analyte monitoring features, according to certain embodiments.

At block 470 of method 400, an indication that a first analyte monitoring device is communicatively coupled to a data processing device is received. The first analyte monitoring device includes a first plurality of analyte monitoring features.

At block 475, a first plurality of application features for the first analyte monitoring device is determined. The first plurality of application features is associated with the first plurality of analyte monitoring features. For example, analyte monitoring features may include a feature for performing blood glucose measurements, and the associated first application features may include a feature for displaying recorded blood glucose measurements.

At block 480, the first plurality of application features is enabled on the data processing device for the first analyte monitoring device.

At block 485, an indication that a second analyte monitoring device is communicatively coupled to the data processing device is received. The second analyte monitoring device includes a second plurality of analyte monitoring features. The second plurality of analyte monitoring features includes at least one analyte monitoring feature that is absent from the first plurality of analyte monitoring features.

For example, the first analyte monitoring device may be removed from the data processing device and the second analyte monitoring device coupled to the data processing device. In such case, the RD software initiates operation with the second analyte monitoring device. In some embodiments, the current application may stay active but replace any first device-specific data with second device-specific data (e.g., imported data from the second device, imported or saved profile information, etc.). In other embodiments, the application may reset or restart for operation with the second analyte monitoring device. Any application features from the first plurality of application features that are absent in the second plurality of application features are disabled.

In some embodiments, the data processing device may indicate the device that is being operated using the RD software—e.g., by activating and/or flashing the backlight of the operated device. Other notifications may also be provided to make the user aware of the proper device that is being operated with the software.

In some instances, the second analyte monitoring device may be coupled to the data processing device while the first analyte monitoring device is still coupled. In such case, the RD software may be programmed to operate with one of the devices—e.g., maintain operation with the first device or begin operation with the second device. This may be indicated, for example, by the backlight on the "operated" device remaining lit while the backlight on the "non-operated" device is not activated.

In yet other embodiments where two analyte monitoring devices are simultaneous coupled to the data processing device, the RD software opens a second application window for the second analyte monitoring device that was added. For example, the second application for the second analyte monitoring device runs independent of, and simultaneously with, the first application running for the first analyte monitoring device. The backlight of the device corresponding to the "active" application window may be lit, for example, to indicate the current analyte monitoring device being "operated".

At block 485, a second plurality of application features for the second analyte monitoring device is determined. The second plurality of application features are associated with the second plurality of analyte-monitoring features, and the second plurality of application features includes at least one application feature that is absent from the first plurality of application features. In some embodiments, the at least one analyte monitoring feature that is absent comprises insulin calculation; and the at least one application feature that is absent comprises enabling customization of device settings for insulin calculation. The insulin calculation may be, for example, a bolus calculation or a basal calculation. In other embodiments, the at least one analyte monitoring feature that is absent comprises a ketone body measurement, and the at least one application feature that is absent comprises displaying recorded ketone body measurements.

At block 490, the second plurality of application features is enabled on the data processing device for the second analyte monitoring device. For example, the RD software may import the data from the second In some embodiments, application features from the first plurality of application features that are absent in the second plurality of application features are disabled.

In some embodiments, the first plurality of analyte monitoring features and the second plurality of analyte monitoring features may include a feature for performing blood glucose measurements, and the first plurality of application features and the second plurality of application features include a feature for displaying recorded blood glucose measurements.

In some embodiments, methods may also include receiving an indication that a third analyte monitoring device is communicatively coupled to the data processing device. The third analyte monitoring device includes a third plurality of analyte monitoring features, and the third plurality of analyte monitoring features include at least one analyte monitoring feature that is absent from the first and second plurality of analyte monitoring features. A third plurality of application features for the third analyte monitoring device is determined. The third plurality of application features are associated with the third plurality of analyte-monitoring features, and the third plurality of application features include at least one application feature that is absent from the first and second plurality of application features. And, the third plurality of application features is enabled on the data processing device for the third analyte monitoring device.

Furthermore, in yet further embodiments, the application features from the first plurality and second plurality of application features that are absent in the third plurality of application features are enabled.

In some aspects of the present disclosure, the analyte monitoring device transfers software to the remote data processing device to perform the methods of enabling different application features on a data processing device for analyte monitoring devices with different analyte monitoring features. For example, the analyte monitoring device may comprises a housing, a strip port coupled to the housing, a first processor coupled to the housing; and memory coupled to the housing and electrically coupled to the first processor. The memory includes the instructions stored therein for transfer to and execution by a second processor on a remote data processing device.

Exemplary Systems

Figure 5:
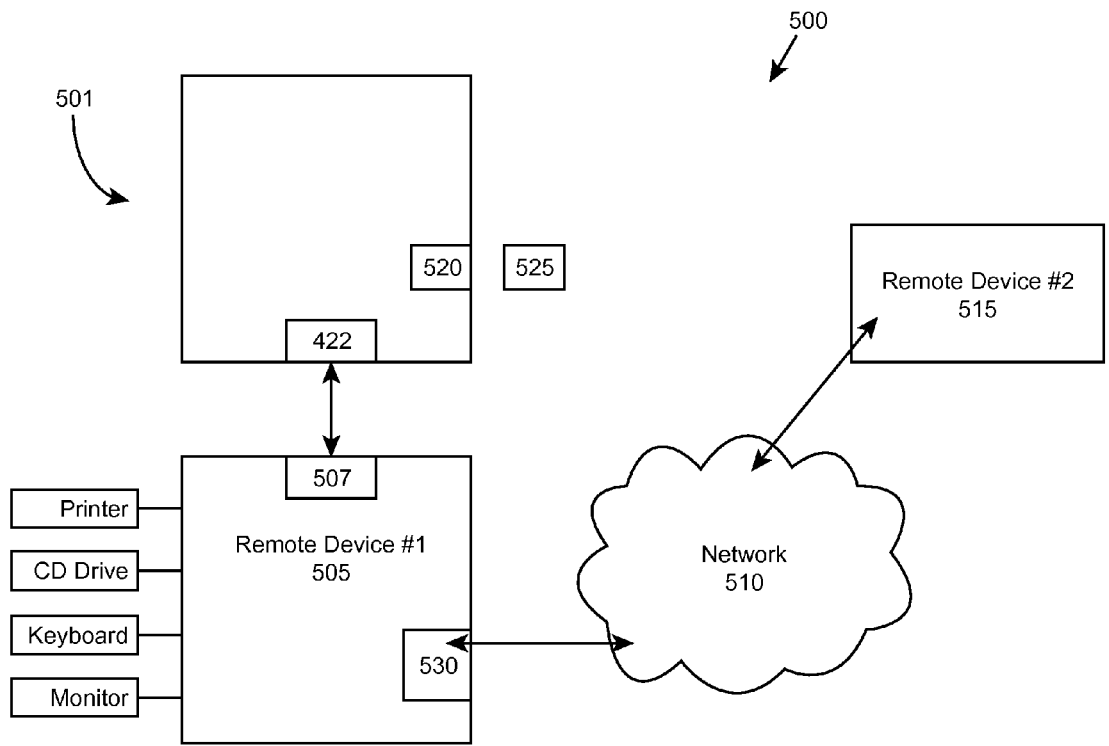
FIG. 5 illustrates a block diagram of a system including an analyte monitoring device and remote data processing device, according to some embodiments.

FIG. 5 illustrates a block diagram of a system including an analyte monitoring device and remote data processing device, according to some embodiments. System 500 is shown to comprising analyte monitoring device 501 communicably coupled to remote device 505. In some instances, as shown, remote device 505 may have network access to a network 510 in which a second remote device 515 is shown coupled to. It should be understood that network 510 may include one or more networks, including LANs, WANs, and/or the internet.

Analyte monitoring device 501 is shown removably coupled to remote device 505 via communication connector unit 422. Communication connector unit, for example, includes a USB plug which couples with a USB receptacle 507 in remote device 505. Remote device 505 may include peripheral devices, such as printer, keyboard, monitor, CD drive, etc. Remote device 505 may also include, as shown, a network interface 530 which connects it to network 510. Remote device 515 is also connected to network 510 and may communicate with remote device 505 via network 510.

The following paragraphs describe system 500 during operation, according to some embodiments. In some instances, the analyte monitoring device described is a glucose monitoring device which measures the glucose concentration level of a blood sample. It should be understood that the description applies equally to other analytes and to other forms of samples.

In use, analyte monitoring device 501 receives a test strip 525 for measuring an analyte level of a sample applied to test strip 525. Test strip 525 is received at strip port unit 520. Analyte monitoring device 501 performs a measurement computation on the sample and the user can view the measurement reading on, for example, a touchsreen display (not shown). The user may also be presented with a menu on the touchscreen display to view and select—e.g., menus for storing data, downloading data, performing bolus calculations based on the measurement, etc.

The user may couple the analyte monitoring device 501 to remote device 505 (e.g., a personal computer) via a communication connector unit. For example, the user may decide to store the measurement data and then choose to download stored test data (including stored measurement readings) to a remote device 505.

Analyte monitoring device 501 may then be coupled to remote device 505 via communication connector unit 422. Communication connector unit 422 may, for example, include a USB plug which couples to a USB receptacle 507 on remote device 505.

In some instances, the analyte monitoring device 501 may be powered by the remote device 505 when coupled via the communication connector unit 422. In such case, the user would couple the analyte monitoring device 501 to the remote device 505 and then insert test strip 525 into the strip port 520 to take a measurement reading. In some instances, the analyte monitoring device includes its own power source, such as button or AAA-size batteries, for example, and is not powered by the remote device 505.

In some instances, the analyte monitoring device may be "locked" or prevented from performing a test while coupled to the remote device 505. For example, medical device regulations such as high voltage isolation testing may be required if the analyte monitoring device is configured to perform tests while coupled to a remote device. Thus, "locking" or preventing the analyte monitoring device from performing a test while coupled to the remote device allows the analyte monitoring device to not be subjected to the additional testing, if so desired.

In some aspects, the analyte monitoring device 501 may initiate a user interface application (e.g., RD software) to execute on the analyte monitoring device, and/or the remote device 505 when coupled to the remote device 505. The user interface application may be stored in a memory unit on the analyte monitoring device 501, for example. In some aspects, the user is not required to have previously loaded software on the remote device 505 to operate with the analyte monitoring device 501. In some aspects, the analyte monitoring device may be configured to initiate the user interface application automatically upon coupling to the remote device. It should be understood that the user interface application may be configured to be compatible with various hardware systems (e.g., PC, MAC) and various operating systems (e.g., Windows, MAC OS, Linux).

The user interface application may include, for example, diabetes management related applications. The user interface application may provide a variety of menus, selections, charts, alarms, reminders, visual indicators, etc. For example, the user may be presented with menus and options, such as whether to take a measurement reading, to view stored measurement readings, to store data, to download data, to perform bolus calculation based on the measurement, etc.

The user interface program may, for example, allow the user to perform the following steps: (1) create a replica of the test data stored on the analyte monitoring device 501, on the remote device 505; and (2) synchronize test data from the analyte monitoring device 501 to the database on the remote device 505. Meter settings and/or user settings/preferences from the analyte monitoring device may also be included in the test data and synchronized with the remote device. Date and time for the remote device 505 and analyte monitoring device 501 may also be synched.

To read test data from the analyte monitoring device 501 and write it to the remote device 505, it is recognized herein that data in the remote device may be organized into tables, which may be organized into records, which may be broken down into predefined fields. Similarly, at some level data will be organized into records with a consistent field structure on the analyte monitoring device 501. The user interface application may read test data from the analyte monitoring device and write it out to tables on the remote device 505. The user interface application may also read data from table in the remote device 505 and write them out to the analyte monitoring device 501. Various types of data conversion may be used. For example, data residing in fields in the analyte monitoring device may be converted from the format it exists in the analyte monitoring device to a format compatible with the remote device, and vice versa. The logical structure of the records in the two systems may be different.

Remote device 505 may include peripheral devices, such as printer, keyboard, monitor, CD drive, etc. Remote device 505 includes a network interface which connects it to network 510 (e.g., the internet). The user interface application may provide the user with the option to view test data on the monitor, to store test data on storage media (e.g., CD-ROM, memory card, etc.), further analyze and/or manipulate test data, transmit data to another device), and/or print out test data such as charts, reports, etc., on the printer.

As shown, remote device 505 may also include a network interface 530 (e.g., network interface card (NIC), modem, router, RF front end, etc.) used to connect the remote device 505 to network 510. For example, in some aspects, analyte monitoring device 501 may couple via a USB connection to the remote device which may be a personal computer or laptop connected to the internet using a wireless modem and/or router. In some aspects, analyte monitoring device 501 may couple via a micro USB connection to a remote device 505 which is a smartphone having an RF front end to access a mobile network. The user interface application may provide a user interface for using the network connection of the remote device 505—e.g., to forward test data to a physician, hospital, health provider, and/or other third party located at a second remote device 515 on network 510. Appropriate action may then be taken by the receiving party at the second remote device 515.

Referring back to FIG. 5, the analyte monitoring device may include a wireless communication unit, for example, which may include, for example, a receiver and/or transmitter for communicating with another device, e.g., remote device 505, a medication delivery device, and/or a patient monitoring device (e.g., a continuous glucose monitoring device or a health management system, such as the CoPilot™ system available from Abbott Diabetes Care Inc., Alameda, Calif.), etc. The wireless communication unit may be configured to wirelessly communicate using a technology including, but not limited to, radio frequency (RF) communication, Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM), etc. In some aspects, the wireless communication unit is configured for bi-directional radio frequency (RF) communication with another device to transmit and/or receive data to and from the analyte monitoring device 501.

In some aspects, the wireless communication unit may be used to communicate with a remote device as described above for the communication connector unit. In some aspects where the analyte monitoring device includes a communication connector unit, the wireless communication unit may replace or provide an optional channel of communication for the functions provided by the communication connector unit discussed above. Referring back to FIG. 5, analyte monitoring device 501 may be coupled to remote device 505 via a wireless communication unit and provide an optional alternative communication channel with remote device 505. In some aspects, analyte monitoring device 501 may not include a communication connector unit 422, and instead only communicate with the remote device 505 via a wireless communication unit present on analyte monitoring device 501. In some aspects, the analyte monitoring device is configured to receive a program update from a remote device via the wireless communication unit.

In some aspects, the wireless communication module may be configured to communicate with a smartphone (e.g., iPhone, Blackberry, etc). It is typical for smartphones to include various wireless technologies such as Wi-Fi, infrared, Bluetooth®, etc.

In some aspects, the analyte monitoring device may be configured to wirelessly communicate via the wireless communication unit with a server device, e.g., using a common standard such as 802.11 or Bluetooth® RF protocol, or an IrDA infrared protocol. The server device could be another portable device, such as a Personal Digital Assistant (PDA) or notebook computer, or a larger device such as a desktop computer, appliance, etc. In some aspects, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

In some aspects, the wireless communication module is used to communicate with a remote sensor—e.g., a sensor configured for implantation into a patient or user. Examples of sensors for use in the analyte monitoring systems of the present disclosure are described in U.S. Pat. No. 6,175,752; and U.S. patent application Ser. No. 09/034,372, incorporated herein by reference. Additional information regarding sensors and continuous analyte monitoring systems and devices are described in U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,100; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. patent application Ser. No. 10/745,878 filed Dec. 26, 1003 entitled "Continuous Glucose Monitoring System and Methods of Use"; and U.S. Application No. 61/149,639 entitled "Compact On-Body Physiological Monitoring Device and Methods Thereof", the disclosures of each which are incorporated by reference herein.

In some instances, the analyte monitoring device is part of a continuous analyte monitoring system, where a transcutaneously implanted sensor may continually or substantially continually measure an analyte concentration of a bodily fluid. Examples of such sensors and continuous analyte monitoring devices include systems and devices described in U.S. Pat. Nos. 6,175,752, 6,560,471, 5,262,305, 5,356,786, U.S. patent application Ser. No. 12/698,124 and U.S. provisional application No. 61/149,639 titled "Compact On-Body Physiological Monitoring Device and Methods Thereof", the disclosures of each of which are incorporated herein by reference for all purposes.

Accordingly, in some aspects, the analyte monitoring device may be configured to operate or function as a data receiver or controller to receive analyte related data from a transcutaneously positioned in vivo analyte sensor such as an implantable glucose sensor. The analyte monitoring system may include a sensor, for example an in vivo analyte sensor configured for continuous or substantially continuous measurement of an analyte level of a body fluid, a data processing unit (e.g., sensor electronics) connectable to the sensor, and the analyte monitoring device configured to communicate with the data processing unit via a communication link (e.g., using the wireless communication module). In aspects of the present disclosure, the sensor and the data processing unit (sensor electronics) may be configured as a single integrated assembly. In some aspects, the integrated sensor and sensor electronics assembly may be configured as a compact, low profile on-body patch device assembled in a single integrated housing and positioned on a skin surface of the user or the patient with a portion of the analyte sensor maintained in fluid contact with a bodily fluid such as an interstitial fluid during the sensor life time period (for example, sensor life time period including about 5 days or more, or about 7 days or more, or about 14 days or more, or in certain instances, about 30 days or more). In such instances, the on-body patch device may be configured for, for example, RF communication with the analyte monitoring device to wirelessly provide monitored or detected analyte related data to the analyte monitoring device based on a predetermined transmission schedule or when requested from the analyte monitoring device. Predetermined transmission schedule may be programmed or configured to coincide with the analyte sample detection by the analyte sensor (for example, but not limited to including once every minute, once every 5 minutes, once every 15 minutes). Alternatively, the analyte monitoring device may be programmed or programmable to acquire the sampled analyte data (real time information and/or stored historical data) in response to one or more requests transmitted from the analyte monitoring device to the on-body patch device.

In some aspects, wireless communication module of the analyte monitoring device includes an RF receiver and an antenna that is configured to communicate with the data processing unit, and the processor of the analyte monitoring device is configured for processing the received data from the data processing unit such as data decoding, error detection and correction, data clock generation, and/or data bit recovery.

In operation, the analyte monitoring device in some aspects is configured to synchronize with the data processing unit to uniquely identify the data processing unit, based on, for example, an identification information of the data processing unit, and thereafter, to periodically receive signals transmitted from the data processing unit associated with the monitored analyte levels detected by the sensor.

In some aspects, the analyte monitoring device may also be configured to operate as a data logger, interacting or communicating with the on-body patch device by, for example, periodically transmitting requests for analyte level information from the on-body patch device, and storing the received analyte level information from the on-body patch device in one or more memory components.

In some aspects, when the analyte monitoring device is positioned or placed in close proximity or within a predetermined range of the on-body patch device, the RF power supply in the analyte monitoring device may be configured to provide the necessary power to operate the electronics in the on-body patch device, and accordingly, the on-body patch device may be configured to, upon detection of the RF power from the analyte monitoring device, perform preprogrammed routines including, for example, transmitting one or more signals to the analyte monitoring device indicative of the sampled analyte level measured by the analyte sensor. In one aspect, communication and/or RF power transfer between the analyte monitoring device and the on-body patch device may be automatically initiated when the analyte monitoring device is placed in close proximity to the on-body patch device. Alternatively, the analyte monitoring device may be configured such that user intervention, such as a confirmation request and subsequent confirmation by the user using, for example, the display and/or input components of the analyte monitoring device, may be required prior to the initiation of communication and/or RF power transfer between the analyte monitoring device and the on-body patch device. In a further aspect, the analyte monitoring device may be user configurable between multiple modes, such that the user may choose whether the communication between the analyte monitoring device and on-body patch device is performed automatically or requires a user confirmation.

Figure 6:
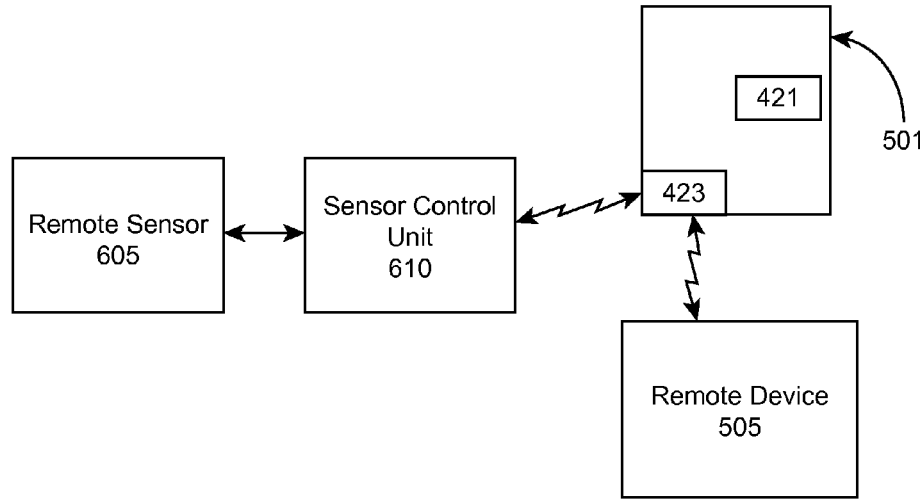
FIG. 6 illustrates an analyte monitoring device used with a remote sensor, according to some embodiments.

FIG. 6 illustrates an analyte monitoring device used with a remote sensor, according to some embodiments. Sensor 605 may be configured for implantation (e.g., subcutaneous, venous, or arterial implantation) into a patient. The sensor 605 is coupled to sensor control unit 610 which is typically attached to the skin of a patient. The sensor control unit 610 operates the sensor 605, including, for example, providing a voltage across the electrodes of the sensor 605 and collecting signals from the sensor 605. The sensor control unit 610 may evaluate the signals from the sensor 605 and/or transmit the signals to wireless communication unit 423 on analyte monitoring device 501 for evaluation.

In some aspects, the wireless communication unit 423 is configured to receive a signal from a remote sensor using radio-frequency identification (RFID) technology. This configuration may be used to provide glucose on demand capabilities, in which case when a measurement reading is desired, the analyte monitoring device is brought within close vicinity of the implantable sensor. In some instances, RFID technology may be used in continuous glucose monitoring (CGM) applications.

The analyte monitoring device 501 processes the signals from the on-skin sensor control unit 610 to determine the concentration or level of analyte in the subcutaneous tissue and may display the current level of the analyte via display unit 421. Furthermore, the sensor control unit 610 and/or the analyte monitoring device 501 may indicate to the patient, via, for example, an audible, visual, or other sensory-stimulating alarm, when the level of the analyte is at or near a threshold level. For example, if glucose is monitored then an alarm may be used to alert the patient to a hypoglycemic or hyperglycemic glucose level and/or to impending hypoglycemia or hyperglycemia.

The analyte monitoring device 501 may perform a variety of functions, including for example: modifying the signals from the sensor 605 using calibration data and/or measurements from a temperature probe (not shown); determining a level of an analyte in the interstitial fluid; determining a level of an analyte in the bloodstream based on the sensor measurements in the interstitial fluid; determining if the level, rate of change, and/or acceleration in the rate of change of the analyte exceeds or meets one or more threshold values; activating an alarm system if a threshold value is met or exceeded; evaluating trends in the level of an analyte based on a series of sensor signals; therapy management (e.g., determine a dose of a medication, etc.); and reduce noise or error contributions (e.g., through signal averaging or comparing readings from multiple electrodes); etc. The analyte monitoring device may be simple and perform only one or a small number of these functions or the analyte monitoring device may perform all or most of these functions.

Analyte monitoring device 501 may communicate with a remote device 505 via communication connector unit 422, and/or wireless communication unit 423, and/or a second wireless communication unit (not shown), as described earlier. It should also be understood that the analyte monitoring device may be configured with one or more wireless communication units.

Software on the Data Processing Device

In some aspects of the present disclosure, software is loaded and launched on a remote data processing device to operate with a coupled analyte monitoring device. The software may include one or more GUI's for communicating with the analyte monitoring device. It should be appreciated a GUI may be used to represent one or more of graphical elements displayed on the display of the remote device for interfacing with the user. Thus, "graphical user interface" or "GUI" may encompass the entire display, an application window, pop-up windows, menus, progress and status bars, buttons, etc.

In some aspects of the present disclosure, the RD software provides a meter mode to provide access to settings and functions that are used to setup and control the analyte monitoring device. The RD software may also provide a meter setup mode to guide the user through the initial setup of the analyte monitoring device. The RD software may provide a reports mode to provide access to settings and function for creating, viewing, saving, and/or printing various reports. In addition, the RD software may provide a reports setup mode to guide a user through the initial reports setup and creation process. The RD software may also provide the function for users to export data from the analyte monitoring device—e.g., as a tab-delimited file or other spreadsheet-compatible format. In some instances, the RD software may provide functions for providing help documents, tutorials, etc. to the user. The RD software may provide functions for checking for software update and for acquiring updates. For example, checks may be automatically initiated and/or initiated by the user. In some instances, the software updates may be checked for and acquired via a network connection on the remote device.

In some embodiments, the RD software provides a user interface to manage and/or control features related to the analyte monitoring device. In some aspects, the RD software provides an interface to manage and/or control features related to generated reports. For example, the RD software provides a reports mode for creating, editing, viewing, printing, and for performing any other functions associated with report generation and management.

Different types of reports may be generated. For example, FIGS. 7A-7F illustrate various types of reports, according to certain embodiments. It should be appreciated that the reports illustrated are exemplary and should not be interpreted as limiting. For the sake of clarity and brevity, the various reports are briefly described. Further details regarding various reports that may be implemented with the software is described in U.S. patent application Ser. No. 11/146,897, filed on Jun. 6, 2005, and U.S. Provisional Application Nos. 61/451,488, filed Mar. 10, 2011; and 60/577,064, filed Jun. 4, 2004, the entireties of which are incorporated herein by reference.

Snapshot Report:

In some aspects of the present disclosure, a Snapshot report is provided. The Snapshot report captures the overall condition of the patient's health management (e.g., diabetes management). For instance, the report may highlight the key metrics for the user's activities over a specific time period. In some embodiments, the Snapshot report may provide significant pieces of information related to one or more of the following: utilization, glucose levels, events (e.g., hypoglycemic events, ketone events, Hyperglycemic events, etc.), trends, insulin and carbohydrate data, notes taken, etc. Additional details related to the above-described information may be found in U.S. Provisional Patent Application No. 61/451,488, filed on Mar. 10, 2011, the entirety of which is incorporated herein by reference.

Figure 7A:
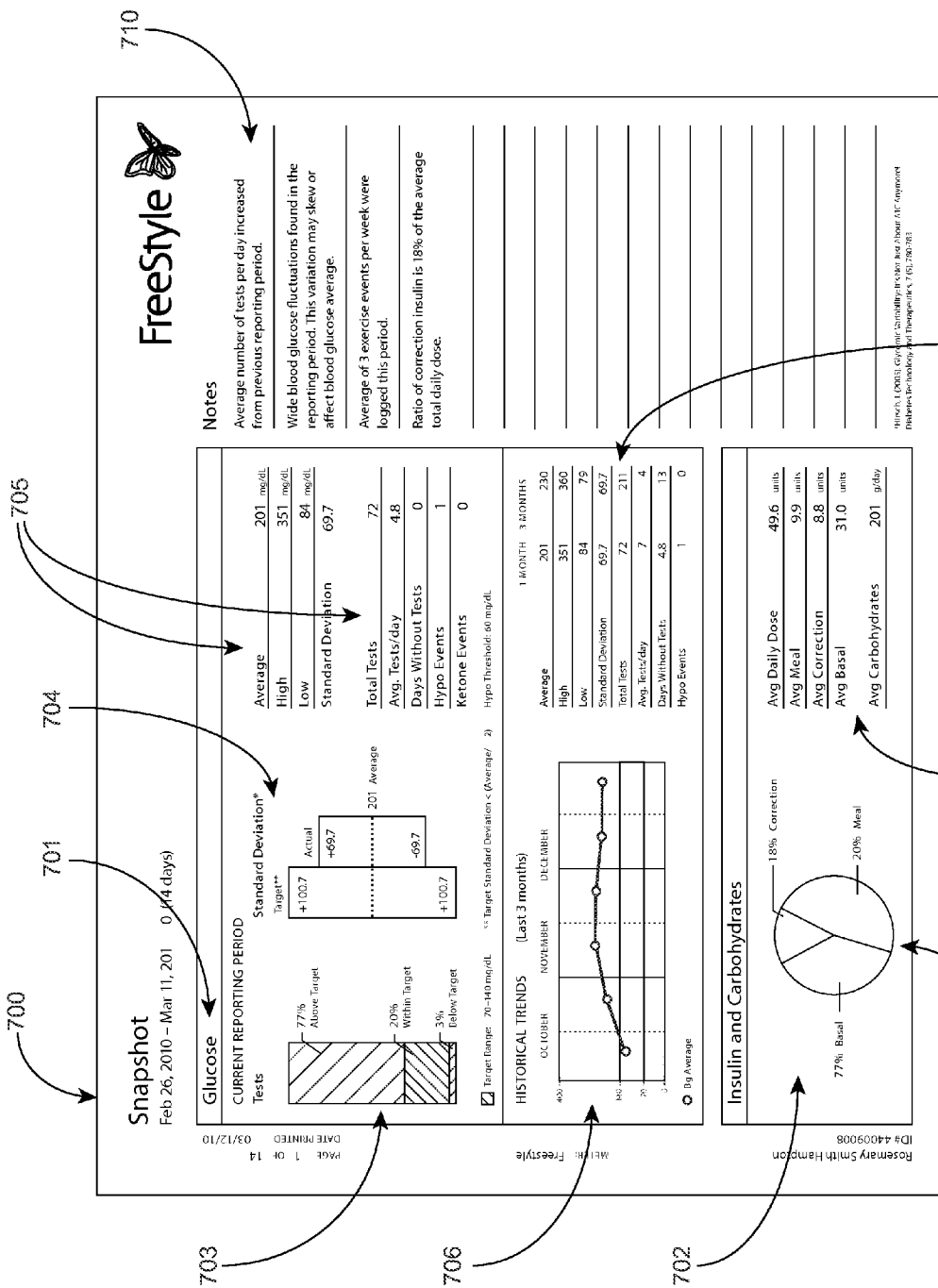
FIG. 7A illustrates a Snapshot report for a specific time frame (e.g., a two week period as shown), according to certain embodiments.

FIG. 7A illustrates a Snapshot report for a specific time frame (e.g., a two week period as shown), according to certain embodiments. Snapshot report 700 includes various pieces of analyte monitoring related information displayed on one report. For example, in the embodiment shown, a glucose section 701 and an insulin and carbohydrates section 702 is provided. Glucose section 701 includes various data related to glucose measurements for the given time period. For example, the glucose section 701 displays an indication 703 for the percentage of tests that were above target, within target, and below target; an indication 704 for standard deviation; and other usage-related indications 705 (e.g., high, low, and average values; total tests; average tests per day; days without tests; hypo events; ketone events; etc.).

In the embodiment shown, indication 704 provides a graphical representation of the standard deviation of actual blood glucose measurements over the two-week time period with respect to an average blood glucose value. The indication 704 also shows a comparison to a target deviation range. In the embodiment shown, the actual standard deviation of +/−69.7 is within the target standard deviation of +/−100.7 from an average value of 201.

Historical trends 706 are also represented within the glucose section 701. The historical trends 706 illustrate trends for past blood glucose measurements. In the embodiment shown, the time-period shown is different than the time period of the snapshot. In other embodiments, the time period may be the same. Other usage and event data may be provided for various time periods, such as shown with indication 707.

Indications 708 and 709 are provided in the insulin and carbohydrate section 702 to represent or display various insulin and carbohydrate related data for the given time period.

Furthermore, a notes section 710 is also provided and conveys various patterns or bits of information for the associated data set for the specific time period. In some instances, the notes are generated by the software based on the user's historical data. In some instances, the notes are notes that have been entered by the user.

Figure 7B:
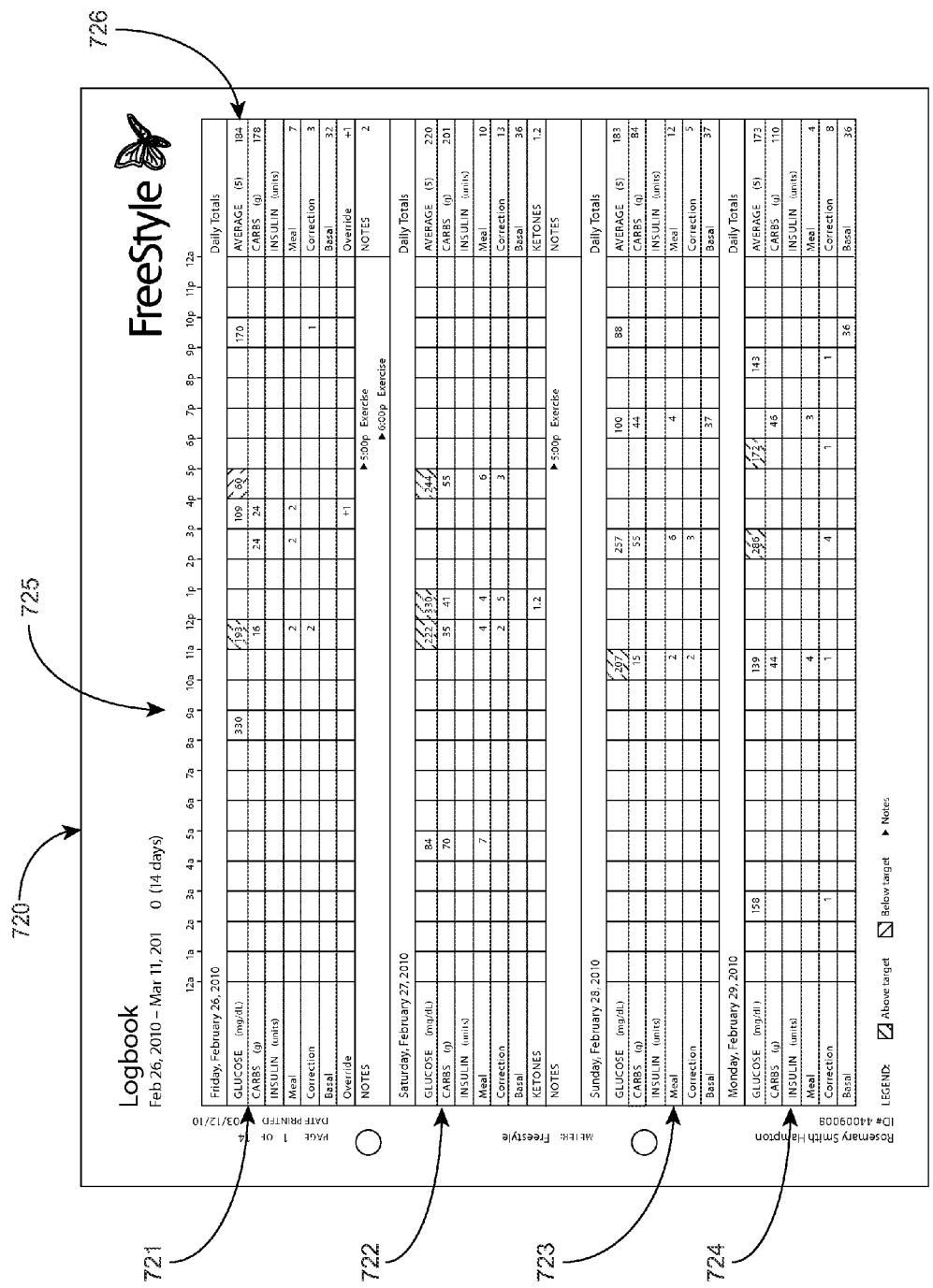
FIG. 7B illustrates a Logbook report, according to certain embodiments.

Logbook Report:

In some aspects of the present disclosure, a Logbook report is provided. A logbook report provides a detailed look at blood glucose readings and, in some cases, other relevant data—e.g., insulin dosage, meals, notes, and ketone events—categorized by time period (e.g., by day). For example, FIG. 7B illustrates a Logbook report, according to certain embodiments. Logbook report 720 presents blood glucose readings in addition to information related to carb, insulin, notes. In FIG. 7B, the logged glucose readings for a selected time period (in this case 2-weeks) is provided in the report. Only one page is shown that comprises data for four days 721, 722, 723, and 724 along a time scale 725 for each day. Each day is broken up in time to identify various readings and other events (e.g., carb entries, insulin entries, notes, etc.). Daily totals 726 are also provided along with indications for measurements that are above or below target.

Figure 7C:
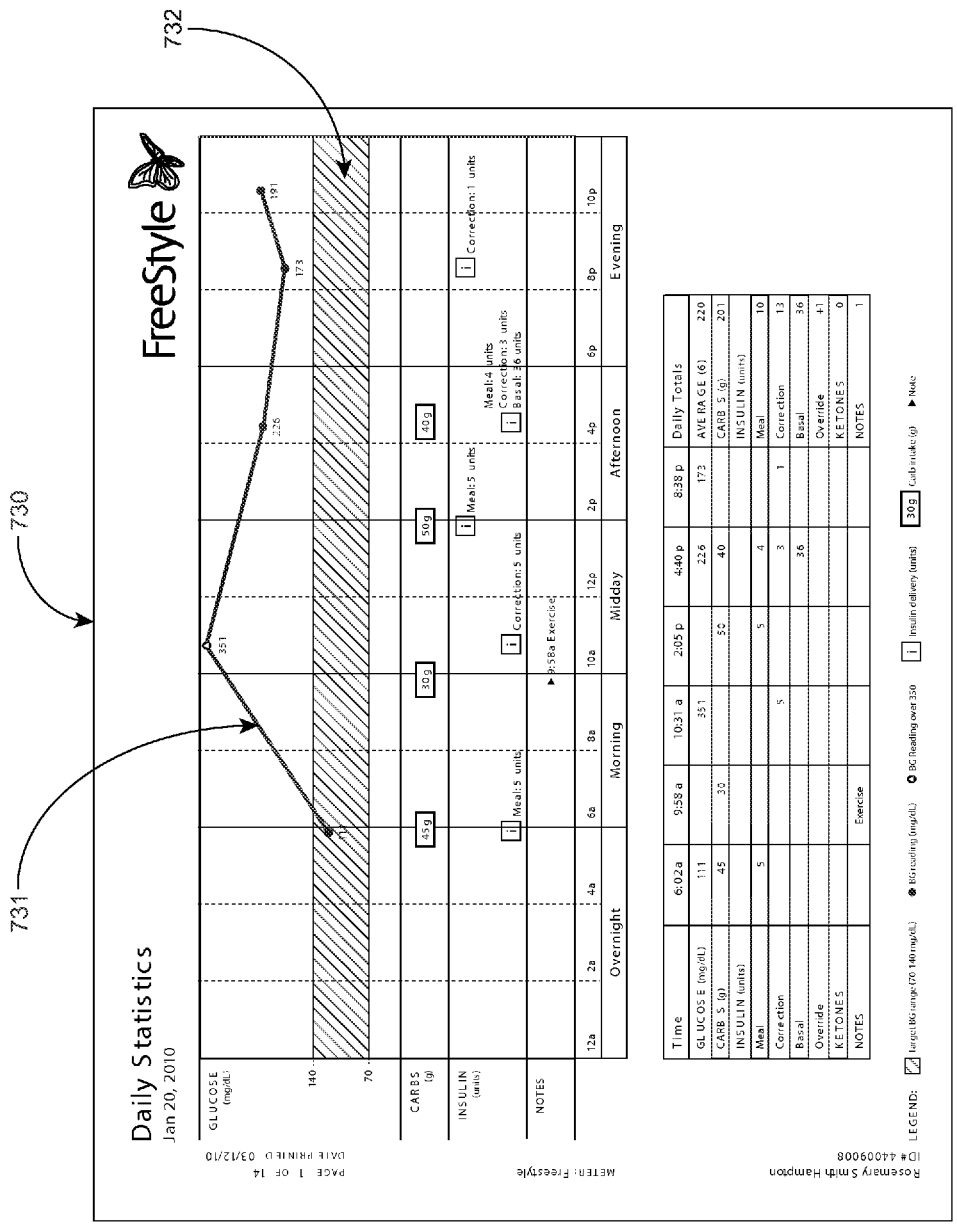
FIG. 7C illustrates a Daily Statistics Report, according to certain embodiments.

Daily Statistics Reports:

In some aspects of the present disclosure, a Daily Statistics report is provided. The Daily Statistics report highlights and details data for glucose readings within a single day. The data may be used to assist in the identification of causes of hypoglycemic events and other abnormalities, for example. For example, FIG. 7C illustrates a Daily Statistics Report, according to certain embodiments. The Daily Statistics Report 730 includes plotted glucose data 731 for times throughout the day. The target range 732 is indicated with shading to provide a quick and easy way to see when the readings are within or outside the target range. Additional recorded information (e.g., carbs, insulin, notes, and ketones) are provided on the graph below each associated reading to remain in the same time-frame context.

Figure 7D:
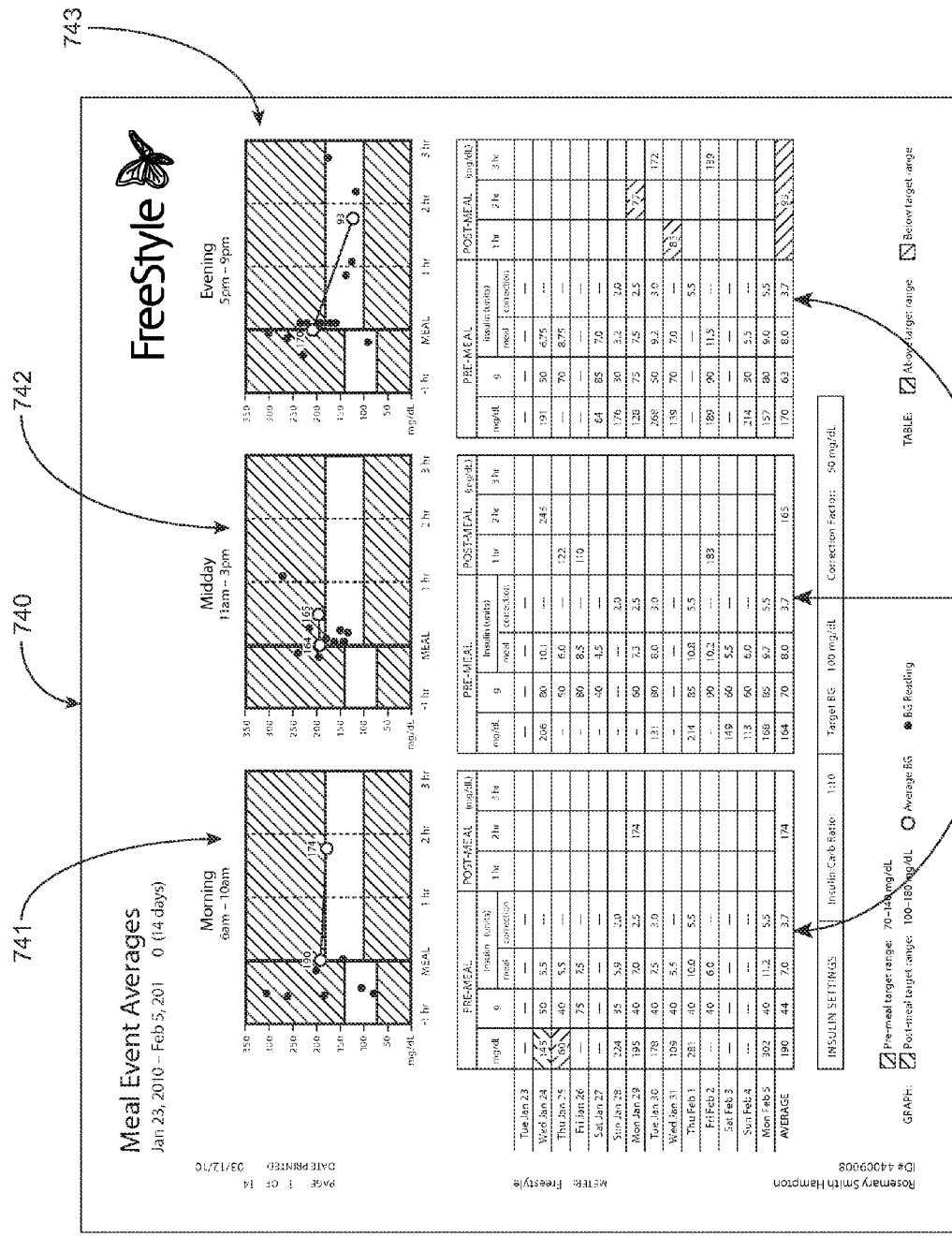
FIG. 7D illustrates a Meal Event Averages report, according to certain embodiments.

Meal Event Averages Reports:

In some aspects of the present disclosure, a Meal Event Averages report is provided. A Meal Event Averages report communicates the rise and fall in glucose levels relative to meals. For example, FIG. 7D illustrates a Meal Event Averages report, according to certain embodiments. Meal Event Averages report 740 presents glucose data before and after meals, over a set timeframe—e.g., in the morning 741, midday 742, and evening 743. A graph is shown, for example, that includes both a pre-meal target range and a post-meal target range in relation to a time a meal occurred. The user's glucose readings are provided on the graph to indicate the user's glucose readings before and after the meal. The graph may be divided into incremental time periods.

Pre-meal insulin and carb information are also provided on the report in charts 744 for each timeframe 741, 742, 743 for each day of the given time period (e.g., two week time period). In addition, other associated information is provided, such as the number of carbs associated with that meal, the amount of insulin (e.g., fast-acting and/or long-acting insulin) taken, etc., may be provided in report 740

Figure 7E:
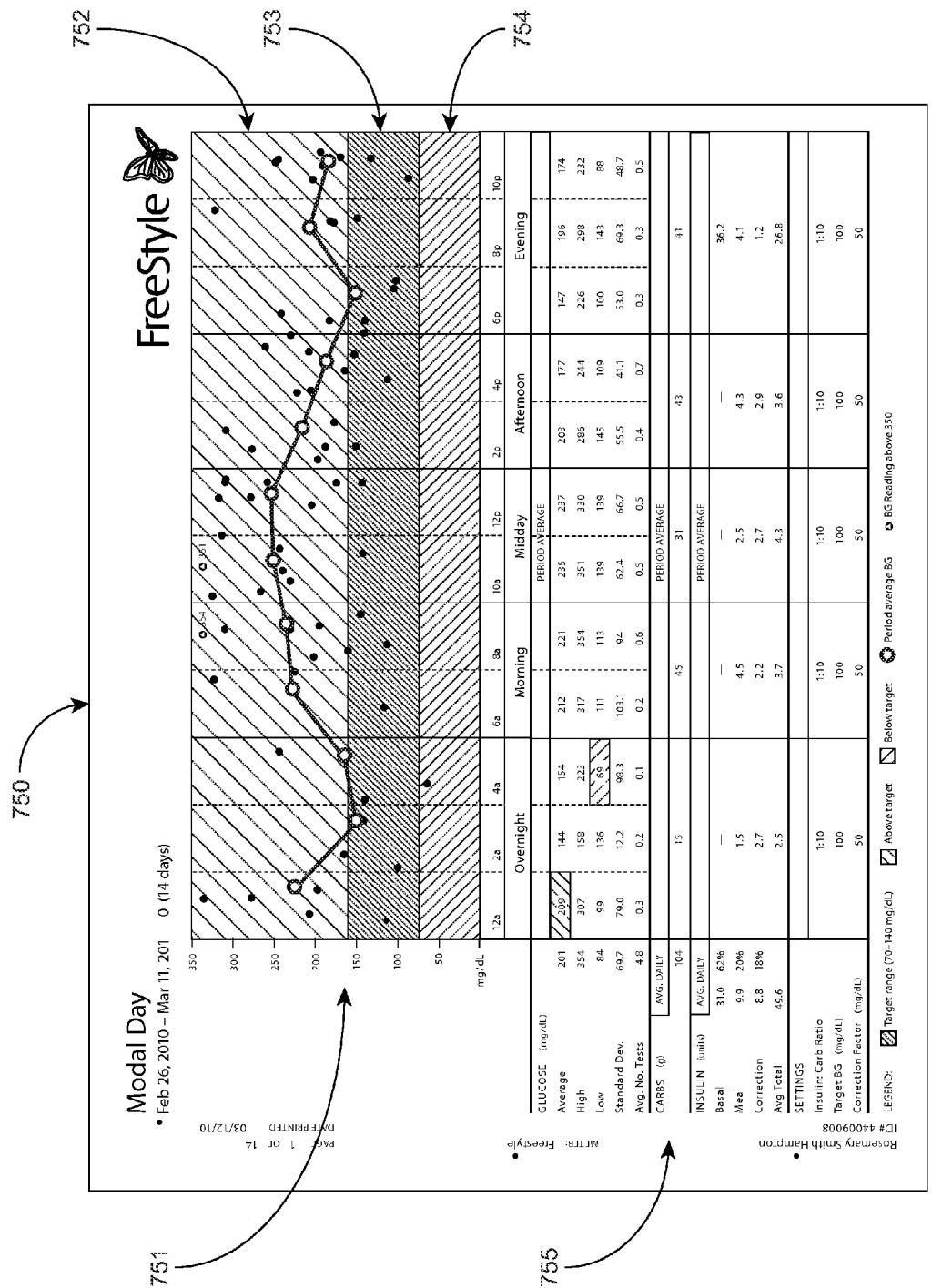
FIG. 7E illustrates a Modal Day report, according to certain embodiments.

Modal Day Reports:

In some aspects of the present disclosure, a Modal Day report is provided. A Modal Day report communicates the trend in glucose levels based across a time period, such as a typical or average day. For example, the embodiment shown in FIG. 7E illustrates a Modal Day report, according to certain embodiments. Modal Day report 750 includes visualization 751 for the trend of average glucose levels across a typical day. Areas containing averages that fall above or below target may be color-coded, as illustrate by different shading in ranges 752,753,754. Tabular data 755 is also provided below the visualization 751 to provide relevant statistics for each time period shown in the visualization 751.

The modal day reports may also include information that represents distribution of the measurement related data. For example, the report may indicate the percentage of measurements that were within a target range, the percentage of measurements that were above the target range, and the percentage of measurements below the target range. As another example, the number of measurements falling within a percentile range for the measurements taken may be indicated in the report—e.g., the number of measurements falling within the top twenty fifth percentile, bottom twenty fifth percentile, etc.

Figure 7F:
FIG. 7F illustrates a Meter Settings report, according to certain embodiments.

Meter Settings Report:

In some aspects, a Meter Settings Report is provided. The Meter Settings Report provides the user with a quick synopsis of pertinent meter settings. Some meter settings may be related to the glucose data—e.g., settings of glucose targets, thresholds, insulin calculation, correction factors, etc. For example, FIG. 7F illustrates a meter settings report, according to certain embodiments. Meter Settings Report 760 comprises sections for profile settings 761, glucose target settings 762, extra settings (e.g., insulin related settings) 763, note settings 764, and reminder settings 765.

It should be appreciated that other reports may also be provided. Additional example reports may include, but are not limited to, Calendar reports (e.g., 30 or 90 day summaries); Usage reports that provide details about the meter utilization to indicate user engagement; Hypoglycemic Events Reports that focus on the hypoglycemic events that occurred in a specific time frame; etc.

Personalization of an Analyte Monitoring Device Using a Remote Data Processing Device In some aspects of the present disclosure, a remote data processing device is used to personalize an analyte monitoring device. The remote device may include software that enables a user to personalize an analyte meter that is coupled to the remote device.

Figure 8:
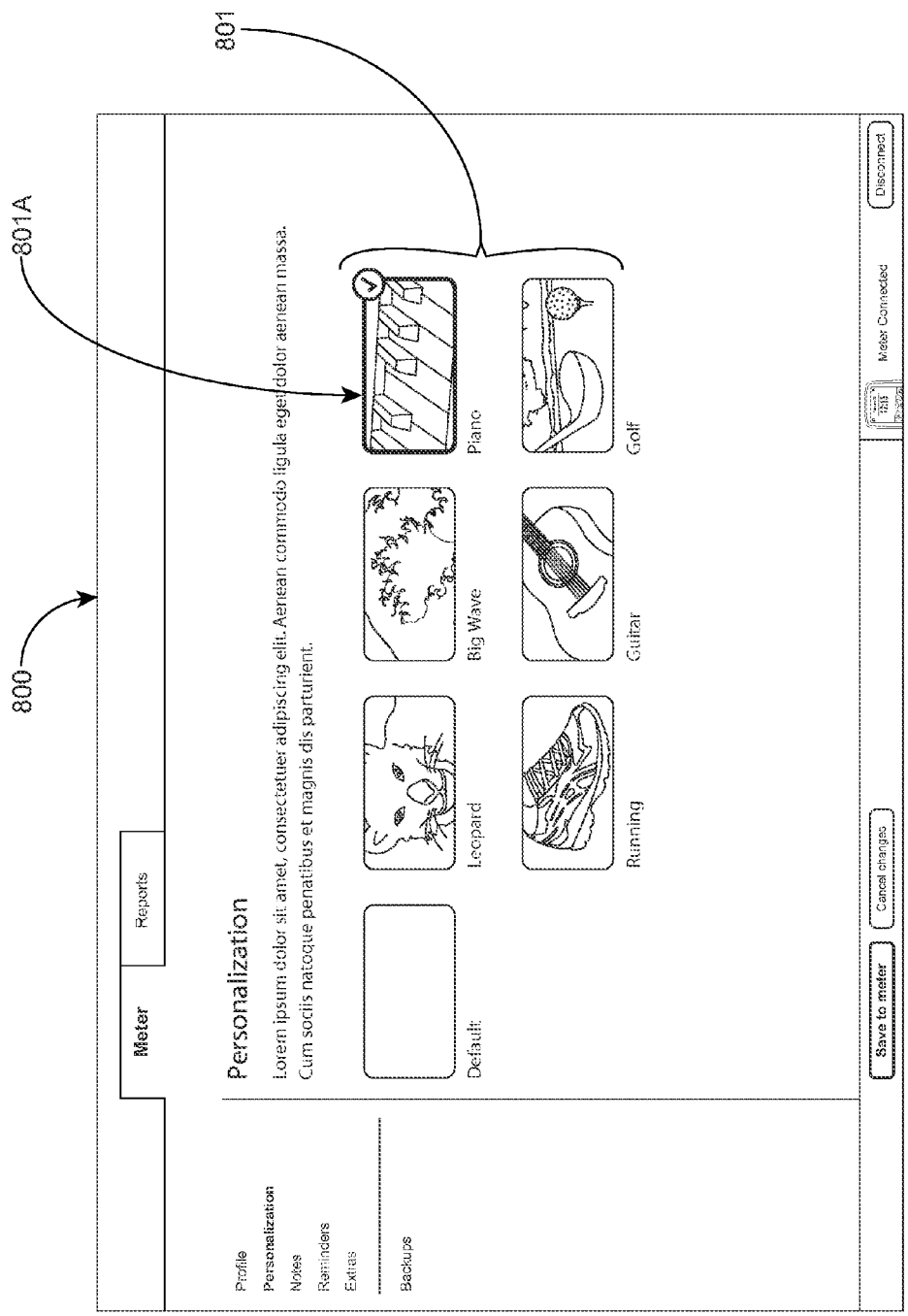
FIG. 8 illustrates an example user interface for personalizing an analyte monitoring device with a remote data processing device, according to certain embodiments.
Figure 9:
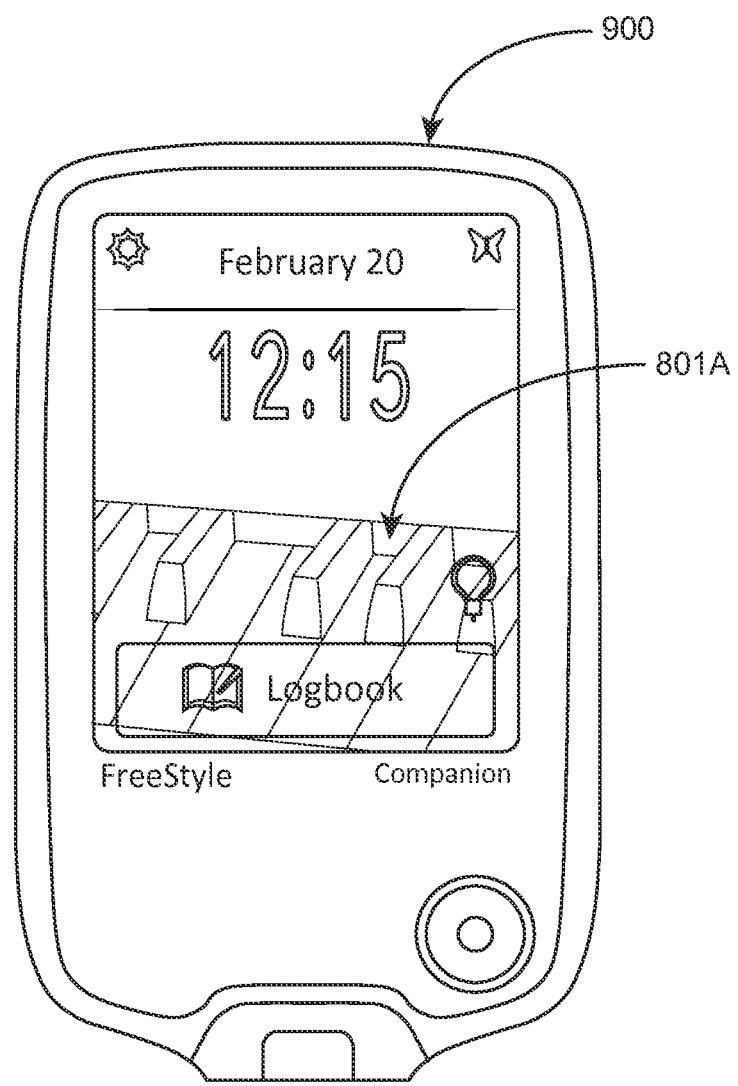
FIG. 9 illustrates an analyte monitoring device configured with a personalized background image, according to certain embodiments.

FIG. 8 illustrates an example user interface for personalizing an analyte monitoring device with a remote data processing device, according to certain embodiments. User interface 800 includes various pre-installed background images 801 that may be selected by a user for display on the analyte monitoring device. The selected background image may be, for example, displayed on the home screen in some instances. In other instances, the analyte monitoring device may be configured to display the background image during a waiting period during a test measurement. As shown, the user has selected the piano image 801A (e.g., the user may be a piano player) for display on the analyte monitoring device. Upon selection, the selected background image 801A is displayed on the analyte monitoring device at the appropriate time and screen, as shown in FIG. 9. FIG. 9 illustrates an analyte monitoring device configured with a personalized background image, according to certain embodiments. After the user selection (and confirmation in some instances) shown in FIG. 8, the analyte monitoring device 900 includes the selected background image 801A displayed on the background of the home screen. In other embodiments, the background image 801A is only shown during a waiting period during a test measurement.

Methods for personalizing an analyte monitoring device with a remote data processing device may comprise receiving an indication that an analyte monitoring device is communicatively coupled to the remote data processing device; and displaying a user interface on the remote data processing device that enables a user to personalize the analyte monitoring device. For example, the user may be able to configure the analyte monitoring device to display a user selected background image. The methods may further comprise receiving input for a user selected background image, and configuring the analyte monitoring device to display the user selected background image.

In some embodiments, the methods comprise displaying a plurality of pre-installed background images on an output display of the remote data processing device so that the user may select one. In some instances, the user may select a different background image that is stored on a memory device or located on the internet, for example, and then uploaded to the device.

In some instances, the methods may comprise personalizing the analyte monitoring device by configuring the analyte monitoring device to display a user selected name. In some instances, user input may be entered from the remote data processing device. In other instances, the user input may be entered from the analyte monitoring device.

Time Based Advanced Programming of an Analyte Monitoring Device

In some aspects, one or more configuration settings and/or user interface settings for the analyte monitoring device may be pre-programmed prior to a future clinical visit and be based on a time period relative to a future event (e.g., a future visit, such as the next future visit). The analyte monitoring device may then be pre-programmed, for example, by the HCP during a current clinical visit by the patient, for a time period in the future based on a future event such as the next clinical visit by the patient. For example, the HCP may pre-program the device for two weeks prior to a future clinical visit.

In some embodiments, the time period begins in the future from the time when the device is pre-programmed. In some instances, the time period begins more than one day after the day the device is pre-programmed, including a time period beginning more than 2 days after the day the device is pre-programmed, for example a time period beginning more than one week after the device is pre-programmed.

Thus, if the time between visits is too long of a time period to gather data, the HCP may set a future time period based on the next clinical visit. For example, if a patient is at a current clinical visit and the next clinical visit is three months later, but three months of data is more than the HCP desires, the HCP may pre-program the device for an appropriately desired time period prior to the next clinical visit—e.g., 2 weeks, 1 month, etc.

In some embodiments, the pre-programming of the device includes beginning to gather data at the specified time period. For example, prior to the beginning of the time period, the user may still use the glucose monitor to monitor his glucose without data being gathered.

In other embodiments, the pre-programming of the device includes pre-programming the device to enter a different data gathering mode when the time period begins. Thus, the device switches to a different data gathering mode when the time period begins. For instances, after the patient leaves the office, the patient will continue with his usual glucose monitoring schedule until the time period established prior to the next scheduled visit. When the time period is reached, the glucose monitor with the advanced programming routine will "switch" the mode of operation and provide additional UI, reminder, and alarm based on the time based advanced programming. The patient may then follow the prescribed reminders and alarms to collect the additional data that the doctor wanted right before the clinical visit in order to better facilitate diagnosis and optimize treatment.

The analyte monitoring device may be pre-programmed to account for a variety of configuration settings and/or user interface settings. This may include instructions or aids for the user (e.g., summary checklists for all the various glucose readings to be obtained in the time period, various reminders and alarms (e.g., reminders to take glucose readings), thresholds, user interface elements, or any other configuration setting and/or user interface settings such as the ones described herein.

The advanced programming of this data "gathering" mode switch can be done at the clinic, for example, as part of the HCP providing new recommendations for the self management routine. In some embodiments, the RD software is used to manage data analysis and therapy change in the clinic (e.g., to pre-program the device) and can be used to provide a more user friendly tool to program the device. For example, the HCP may plug the analyte monitoring device into a computer causing the RD software application to launch on the computer, subsequently pre-programming the device via the computer. In some embodiments, the time based advanced programming can be done on the analyte monitoring device itself, through the corresponding configuration graphical user interface presented on the device.

The time period may be preprogrammed into the device as well as any attributes of the data gathering mode that is to be entered during the time period. The time period may include, for example, starting and ending dates in the future, only a starting date in the future, etc. The attributes of the data gathering mode may, for example, include the adding of three more SMBG readings 2 hours after each meal, at approximately 10 am, 2 pm, and 9 pm. The attributes may include other relevant thresholds for UI, alarms, and/or reminders that make up the data gathering mode (e.g., reminder only, reminder+alarm, daily checklist, weekly checklist, etc.). Furthermore, in some instances, the time of the next clinical visit may be entered. The time period may, for example, in such case, identify the time period prior to the date entered for the next clinical visit.

It should be appreciated that in some embodiments, more than one future time period may be pre-programmed if desired.

Condition Based Advanced Programming of an Analyte Monitoring Device

In some aspects, one or more configuration settings and/or user interface settings for the analyte monitoring device may be pre-programmed prior to a future clinical visit and be based on a future data condition obtained by the analyte monitoring device prior to the next clinical visit. The discussion above for time based advanced programming applies here to condition based advanced programming, except that the trigger for the entry into the pre-programmed mode is based on the occurrence of a future condition rather than a future time period relative to a future event (e.g., the next clinical visit).

The data condition may be any variety of conditions related to the data taken by the analyte monitoring device. For example, the data condition may be associated with, but not limited to, measurement readings, thresholds, trends, patterns, other events (e.g., meal events, carb level thresholds, exercise events, state of health, etc.), etc. In some instances, the events may be user-entered.

For example, if a HCP finds that a pattern exists where whenever the patient has a pre-prandial glucose of less than 110 mg/dL (e.g., not every meal, but frequently occurring), the patient has a tendency to go low 3 hours after the meal. The HCP may decide to, for example, recommend the patient adjust the bolus calculator recommended meal bolus readings whenever a pre-meal SMBG is below 110 mg/dL, and at the same time pre-program the device to turn on this data gathering feature. If future condition occurs, the device then enters the pre-programmed data gathering mode. The pre-programmed data gathering mode may include configuration settings and/or user interface settings that, for example, provide the user with reminders, alarms, instructions, etc. For example, upon occurrence of the future condition, the data collection mode ay be activated, reminders sent to the patient on what to do (e.g., lower insulin by 2-5%), and alarm the patient regularly to check SMBG after that meal at regular intervals (e.g., 2, 3, 4, and 5 hours after the meal) in order to detect and mitigate potential lows). In some embodiments, the patient would have the option to turn off one or more settings (e.g., the interval alarms described above, etc.). In some embodiments, the settings will be locked so the user cannot change any of the settings.

When the patient leaves the office, for example, he may continue with his normal monitoring schedule and routine and attempt to follow the new dosing algorithm for these meal boluses when his pre-meal BG falls below 110 mg/dL. The condition based pre-programming will be activated upon occurrence of the condition and assist the user, for example, to obtain the additional data. This additional data may then be review by the HCP during the next visit and analyzed to evaluate the new routine.

One or more attributes of the condition based advanced programming may be entered (e.g., via the RD software application launched on a remote device, and/or on the user interface of the analyte monitoring device itself). The detected condition that will trigger the activation of the data gathering mode may be preprogrammed into the device. In some instances, one or more of the following example attributes may be entered: the duration of the data collection activation after the detected condition may also be entered (e.g., number of minutes, hours, days, weeks, etc.); an SMBG reminder schedule and/or other reminder schedule (e.g., one time, recurring every hour, x-hours, daily, weekly, etc.); SMBG alarm schedule and/or other alarm schedule (e.g., one time, recurring every hour, x-hours, daily, weekly, etc.), etc.

Graphical Representation of Insulin on Board

In some aspects, the analyte monitoring device may be configured to graphically represent the amount of insulin remaining in the user's body. Knowing the insulin on board helps to avoid bolus stacking or overlapping of multiple boluses taken by the user. The graphical representation provides a different and more intuitive way to display and present the insulin on board to the user than by presenting a numerical value.

A graphical user interface element may be presented on the display of the analyte monitoring device to indicate the insulin on board (IOB or Bolus on Board). In some embodiments, the insulin on board is represented as a "gauge" to provide the user with an indication as to the amount of insulin remaining in the body. The exact value is not required but rather a general indication as to how much insulin remains. In some instances, the graphical user interface element includes markers to indicate a maximum and minimum amount of insulin along with an indication element of the current amount of insulin remaining in the body (indicated at or between the maximum and minimum).

For example, in some embodiments, the current amount of insulin remaining in the body is represented by a fill-level of the graphical user interface element (i.e., the indication element is the filling). The graphical interface element is thus a fill-level indicator. The graphical element is provided and the amount that the graphical element is filled represents the amount or percentage of insulin remaining in the body. For example, if the graphical element is completely unfilled, then no insulin remains. If the graphical element is completely filled, then 100% of the insulin remains. The user can easily and quickly identify the approximate percentage that the graphical element is filled and thus obtain an approximate understanding of the amount or percentage remaining in the body. FIGS. 10A-10B illustrate an example graphical user interface element that functions as a fill-level indicator, according to some embodiments. Bar 1001 is shown approximately 100% filled and represents the amount of insulin remaining in the body after a bolus was delivered. Bar 1002 is shown approximately 30% filled indicating approximately 30% insulin on board remaining from the amount previously delivered. In the embodiment shown, a bar is shown, however it should be understood that other shapes (e.g., triangles, circles, etc.) and orientations (vertical, horizontal, etc.) may be implemented.

In some embodiments, the graphical user interface element includes markers indicating a maximum and minimum, and the current amount of insulin remaining in the body is indicated by an indicator element between the maximum and minimum graphical indications. The indicator element may be, for example, an arrow pointing to a point between the maximum and minimum. Where the indicator element resides relative to the maximum and minimum indications provides the user with an approximate percentage or value remaining in the body. It should be understood that other forms of indicator elements may be used such as a line, dot, star, icon, or any other form of graphic. For example, the level in the bar in FIGS. 10A-10B may be represented by a single line, and not necessarily "filled".

FIGS. 11A-11B illustrate an example graphical user interface element representing insulin remaining in a body, according to some embodiments. Gauge 2001 is shown approximately 100% filled and represents the amount of insulin remaining in the body after a bolus was delivered. Gauge 2002 is shown approximately 30% filled indicating approximately 30% insulin on board remaining from the amount previously delivered. In some instances, additional identifying markers may be present in the graphical user interface to indicate divisions, approximate values, thresholds, etc. For instance, as shown in FIGS. 11A-11B, three additional identifying markers are present to indicate divisions by quarters (i.e., 25% full, 50% full, and 75% full).

In some aspects of the present disclosure, methods for graphically represent a remaining insulin level in a user body are provided. The methods comprise displaying a first marker on the output display to indicate a maximum amount of insulin; displaying a second marker on the output display to indicate a minimum amount of insulin; and displaying a indication element on the output display to indicate a current amount of insulin in the user body, wherein the positional relation of the indication element to the first and second markers is approximately proportional to the percentage of insulin remaining in the body.

In some embodiments, the indication element may be, for example, a fill-level of a graphical element, wherein the second marker is at one end of the graphical element and corresponds to a zero percent fill-level, and wherein the first marker is at an opposite end of the graphical element and corresponds to a one hundred percent fill-level.

In some embodiments, the graphical element is body-shaped, and wherein the second marker is at a foot-end of the body-shaped graphical element, and wherein the first maker is at a head-end of the body-shaped graphical element. For example, FIGS. 12A and 12B illustrate a graphical element representing insulin in the body, according to certain embodiments. Graphical element 1200 is a body-shaped graphical element wherein the element is filled from the foot end 1202 to the head end 1201 of the element. The percentage of the element filled is proportional to the percentage of insulin remaining in the body.

In other embodiments, the indication element is an arrow pointing to a position at or between the first marker and the second marker. In some instances, the methods comprise displaying one or more identifying markers between the first marker and second marker to represent divisions, approximate values, or thresholds.

Line Graph Data Representation for Glucose-on-Demand Systems

In some aspects, the analyte monitoring device may be configured without memory for storing measured glucose values. For example, an on-body unit may not record measurements, and the user initiates a read when a measurement reading is desired. For example, analyte monitoring related data may be provided during an on-demand reading. Such analyte monitoring related data may include magnitude data, as well as rate-of-change data, for the on-demand measurement.

In some aspects of the present disclosure, methods of providing a graphical representation of such on-demand readings are provided. The methods may include outputting a graphical representation of the analyte monitoring related data that includes graphical elements plotted at locations corresponding to the magnitude values of the on-demand readings. Furthermore, the graphical elements visually represent the rate-of-change data for each on-demand reading. For example, in some embodiments, the graphical element may be an arrow that is plotted at the corresponding magnitude value on a chart. The direction or orientation of the arrow may indicate the rate-of-change of that specific on-demand reading. For example, an upward pointing arrow may indicate an upward trend. Further, the degree of incline of the upward pointing arrow may indicate the degree of the upward trend. Similarly, downward pointing arrows may represent a downward trend. In some instances, the arrows may match the arrows presented on the user interface of the analyte monitoring device. In other embodiments, a color or size of the graphical element may indicate the direction and/or degree of rate-of-change.

Figure 13A:
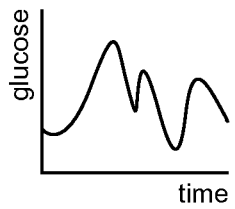
FIG. 13A illustrates a plot for continuous glucose measurements.
Figure 13B:
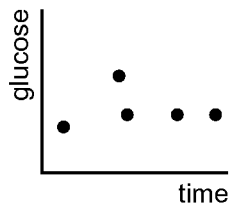
FIG. 13B illustrates a plot of magnitudes for on-demand measurements for the same glucose pattern.
Figure 13C:
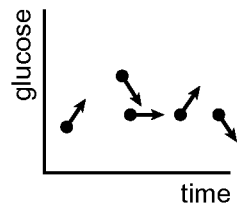
FIG. 13C illustrates a plot of magnitudes and rate-of-change data, according to certain embodiments.

FIG. 13A illustrates a plot for continuous glucose measurements. FIG. 13B illustrates a plot of magnitudes for on-demand measurements for the same glucose pattern. As shown, FIG. 13B does not provide the user with much information in addition to the actual glucose value readings. Trending and other patterns are not discernable. In FIG. 13C, magnitude data of the on-demand measurements are provided in addition to rate-of-change data. As shown, an arrow is illustrated at each on-demand reading and the location of the arrow represents the magnitude of the reading. Furthermore, the direction of the arrow correlates to the rate-of-change of the reading at that instant. Furthermore, the degree of the arrow conveys the degree of the rate-of-change—e.g., with steeper pointing upward arrows and downward arrows correlating to a larger rate-of-change in the corresponding direction. Thus, in FIG. 13C, the user is able to discern whether glucose values are stable, rising, or falling.

In another aspect, the glucose rate of change information and the timing between glucose values is used to determine rules for when a line is drawn on the graph connecting subsequent glucose values. For example, if two values are taken in close proximity (e.g., less than 30 minutes apart) and the rate-of-change observed at the time of the first reading indicated a rising trend and the second glucose value was greater than the first, then the points may be connected by a line. The line may be, for example, dotted, color coded, or otherwise represented to indicate to the user that it is a "fit" to the data and does not represent additional measured glucose values. Alternatively, an autoregressive approach is used to connect the points when there is sufficient data density and when the subsequent glucose value falls within the range predicted by the autoregressive mode.

In some embodiments, a standard spline technique is used to connect the dots with curves instead of straight lines. Other model based approaches are also possible—e.g., that use both glucose and glucose rates to produce a continuous profile. For example, a standard stochastic state observer may be used to predict forward from one point and/or predict backward from the next point. In this way, it may provide the prediction error forward and backward. The forward and backward predication curves between the two points may be combined as one weighted prediction error. For example, the prediction error may be represented by the following equation:

$$F(t)=[P^+(t)*(1/E^+(t))^2+P^-(t)*(1/E^-(t))^2]/[(1/E^+(t))^2+(1/E^-(t))^2]$$

Wherein F(t) is the resulting line, P+(t) is the forward prediction line; P⁻(t) is the backward prediction line; E⁺(t) is the forward prediction error; E⁻(t) is the backward prediction error.

Figure 14:
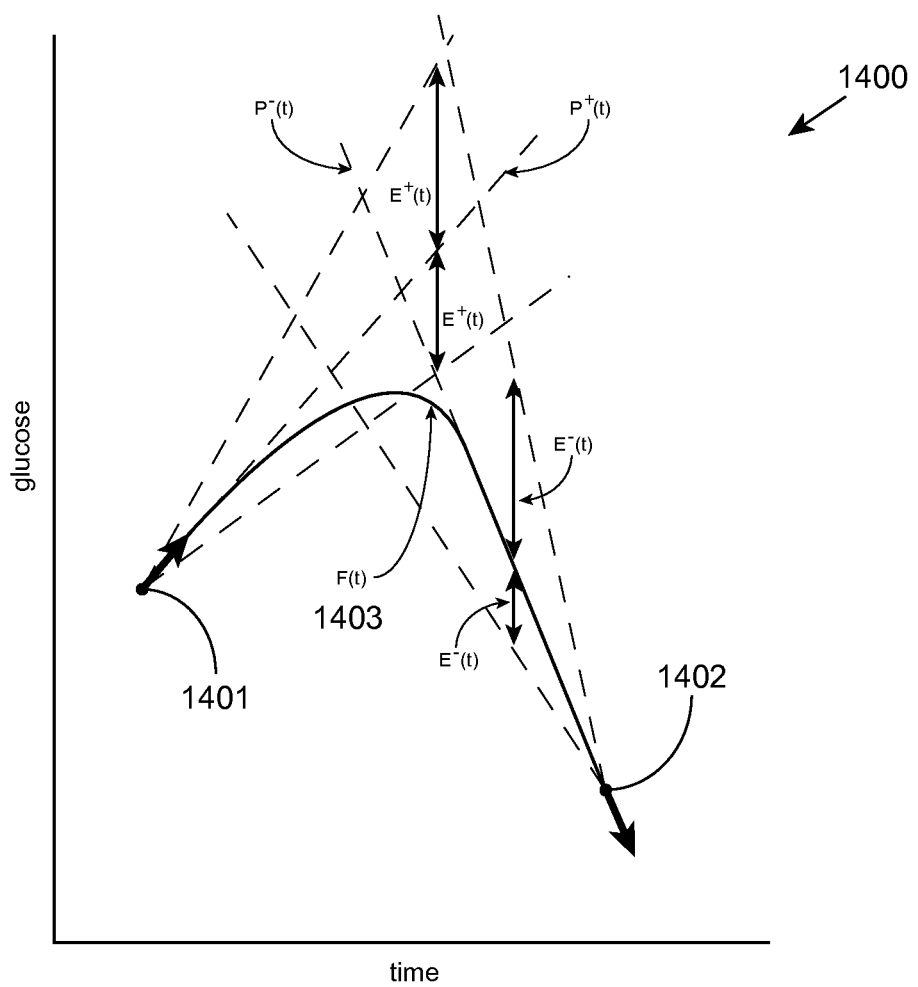
FIG. 14 illustrates a plot using forward and backward prediction errors to provide a line between plots, according to certain embodiments.

FIG. 14 illustrates a plot using such a prediction error, according to certain embodiments. As shown, data for on-demand readings 1401 and 1402 are provided on a graph 1400. Forward prediction line P⁺(t) and backward prediction line P⁻(t), and corresponding forward prediction error E⁺(t) and backward prediction error E⁻(t) are used to provide resulting line 1403 between the two points 1401 and 1402. If the error E⁺(t) or E⁻(t) exceeds a predetermined threshold, for example 10 mg/dL or 30 mg/dL, then a line connecting the points won't be drawn but rather the gap will be left.

Protection of Access to Features on an Analyte Monitoring Device

In some aspects, the analyte monitoring device may be configured to prevent the user from accessing specific features of the analyte monitoring device. The user may be blocked access from specific features for any variety of reasons, such as proficiency of the subject matter related to the feature, non-applicability of the feature to the patient, etc. For example, many advanced features such as bolus calculators and basal titration algorithms require a user to be proficient in knowledge and management of their disease state in order to be used safely and effectively. The user may not have the required knowledge or training to use such features properly.

In some aspects, the analyte monitoring device may be configured with software protection mechanisms to ensure the user does not have access to specific features. In some instances, the software protection mechanisms may be implemented to confirm that the user is qualified to use the feature. The software protection mechanism may implement a test to certify that the user is qualified to use the feature. In some instances, the software protection mechanism may present the user with a series of one or more questions that demonstrates the user is proficient in the subject matter related to the feature to be unlocked. For example, a protection screen that allows access to a bolus calculator feature may check that a user understands carb counting (e.g., by asking them to answer one or more questions on the number of carbs in a slice of bread), and/or correction factor (e.g., by asking one or more questions related to correction factor), etc. In some instances, the question may be presented in a multiple choice format. In order to provide additional protection against an unqualified user trying to access a feature by randomly guessing answers, the functionality can be locked out after a number of attempts, and unlocked by password, special key, etc.

In some instances, the HCP may confirm the user is qualified to use the feature and unlock access to the feature. For example, the HCP may possess the appropriate password or key necessary to unlock the feature.

It should be understood that techniques introduced herein can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc. The term "logic", as used herein, can include, for example, special purpose hardwired circuitry, software and/or firmware in conjunction with programmable circuitry, or a combination thereof.

The preceding merely illustrates the principles of the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the present disclosure and the concepts contributed by the inventors to furthering the art, and are to be construed as being without limitation to such specifically recited examples and conditions. Moreover, all statements herein reciting principles, aspects, and aspects of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary aspects shown and described herein. Rather, the scope and spirit of present disclosure is embodied by the appended claims.

What is claimed is:

1. A method for selectively displaying features of a first analyte monitoring device and a second analyte monitoring device, comprising:

coupling a first analyte monitoring device or a second analyte monitoring device to a computer via a communication interface, wherein the first analyte monitoring device comprises a first plurality of analyte monitoring features selected from performing blood glucose measurements, performing blood ketone measurements, performing carbohydrate measurements, performing bolus insulin calculations, performing basal insulin calculations, and performing device personalization; and the second analyte monitoring device comprises a second plurality of analyte monitoring features selected from performing blood glucose measurements, performing blood ketone measurements, performing carbohydrate measurements, performing bolus insulin calculations, performing basal insulin calculations, and performing device personalization;

receiving, with a processor of the computer, an indication that the first analyte monitoring device is communicatively coupled to the computer via the communication interface;

determining, with the processor, a first plurality of application features corresponding with the first plurality of analyte monitoring features for the first analyte monitoring device;

initiating, with the processor, a user interface application and display the first plurality of application features on a display of the computer;

receiving, with the processor, an indication that the second analyte monitoring device is communicatively coupled to the computer via the communication interface;

determining, with the processor, a second plurality of application features corresponding with the second plurality of analyte monitoring features for the second analyte monitoring device, and the second plurality of application features:
  (a) includes an application feature that is absent from the first plurality of application features, or
  (b) does not include an application feature present in the first plurality of application features; and modifying, with the processor, the user interface application to display on the display the application feature that is absent from the first plurality of application features, if a determination is made that the second plurality of application features include an application feature that is absent from the first plurality of application features, or modifying, with the processor, the user interface application to no longer display on the display the application feature that is present in the first plurality of application features but not in the second plurality of application features, if a determination is made that the second plurality of application features does not include the application feature present in the first plurality of application features.

2. The method of claim 1, wherein the second plurality of application features does not include an application feature present in the first plurality of application features and the method further comprises modifying, using the processor, the user interface application to no longer display the application feature that is present in the first plurality of application features absent in the second plurality of application features.

3. The method of claim 1, wherein the analyte is glucose.

4. The method of claim 1, wherein the first plurality of analyte monitoring features and the second plurality of analyte monitoring features include a feature for performing blood glucose measurements, and wherein the first plurality of application features and the second plurality of application features include a feature for displaying recorded blood glucose measurements.

5. The method of claim 1, wherein the at least one analyte monitoring feature that is absent comprises insulin calculation; and wherein the at least one application feature that is absent comprises enabling customization of device settings for insulin calculation.

6. The method of claim 5, wherein the insulin calculation is bolus calculation.

7. The method of claim 5, wherein the insulin calculation is basal calculation.

8. The method of claim 1, wherein the at least one analyte monitoring feature that is absent comprises ketone body measurement, and wherein the at least one application feature that is absent comprises displaying recorded ketone body measurements.

9. The method of claim 1, further comprising:
  receiving an indication, using the processor, that a third analyte monitoring device is communicatively coupled to the computer via the interface, wherein the third analyte monitoring device includes a third plurality of analyte monitoring features, and wherein the third plurality of analyte monitoring features include at least one analyte monitoring feature that is absent from the first and second plurality of analyte monitoring features;
  determining, using the processor, a third plurality of application features corresponding with the third plurality of analyte monitoring features for the third analyte monitoring device, and the third plurality of application features include at least one application feature that is absent from the first and second plurality of application features; and
  modifying, using the processor, the user interface application to display on the display the application feature that is absent from the first and second plurality of application features.

10. The method of claim 9, further comprising modifying, using the processor, the user interface application to no longer display on the display an application feature present in the first and second plurality of application features but absent in the third plurality of application features.

* * * * *